(12) United States Patent
Hwu et al.

(10) Patent No.: US 6,734,014 B1
(45) Date of Patent: May 11, 2004

(54) METHODS AND COMPOSITIONS FOR TRANSFORMING DENDRITIC CELLS AND ACTIVATING T CELLS

(75) Inventors: Patrick Hwu, Rockville, MD (US); Mark Reeves, New York, NY (US); Steven A. Rosenberg, Potomac, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/117,764

(22) PCT Filed: Feb. 7, 1997

(86) PCT No.: PCT/US97/02063

§ 371 (c)(1),
(2), (4) Date: Jan. 7, 1999

(87) PCT Pub. No.: WO97/29183

PCT Pub. Date: Aug. 14, 1997

Related U.S. Application Data

(60) Provisional application No. 60/011,433, filed on Feb. 8, 1996.

(51) Int. Cl.$^7$ .......................... A61K 48/00; C12N 5/02; C12N 15/63; C12N 15/85
(52) U.S. Cl. .................... 435/325; 435/320.1; 435/455; 424/93.2; 424/93.21; 514/44
(58) Field of Search .............................. 435/325, 320.1, 435/455; 424/93.21, 93.2; 514/44

(56) References Cited

FOREIGN PATENT DOCUMENTS

| EP | 0 563 485 A | 10/1993 | ............ C12N/5/08 |
|---|---|---|---|
| WO | WO 93 18137 A | 9/1993 | ............ C12N/5/06 |
| WO | WO 94 16716 A | 8/1994 | ........... A61K/37/00 |
| WO | WO 94 27435 A | 12/1994 | ........... A01N/25/26 |
| WO | WO 95 06120 A | 3/1995 | ........... C12N/15/23 |
| WO | WO 95 34676 A | 12/1995 | ............ C12Q/1/00 |
| WO | WO 97 03703 A | 2/1997 | ........... A61K/48/00 |

OTHER PUBLICATIONS

Rouse et.al.; Induction in Vivo of Primary Cytotoxic T–Lymphocyte Responses with DNA Encoding Herpes Simplex Virus Proteins, 1994, Journal of Virology, vol. 68: 5685–5689.*
Heemskerk et.al.; No. 01227285–9660681(Abstract).*
Drexhage et. al.; Dendritic Cells: Antigen Presenting Cells of T and B Lymphocytes, Ci–204–Ci–207.*
Alijagic et. al.; Dendritic cells generated from peripheral blood transfected with human tyrpsomase induce specific T cell activation, 1995, Eur. J. Immunol. 25: 3100–3107.*
Holland et. al.; Differentiation of Human Hematopoietic Cells Increases Expression of a Gene Transferred by a Retroviral Vector; 1989, Journal of Leukocyte Biology 46: 221–229.*
Siena et. al.; Massive ex vivo generated of functional dendritic cells from mobilized CD34 blood progenitors for anticancer therapy, 1995, Experimental Hematology 23: 1463–1471.*
Bakker, A.B., et al., "Generation of antimelanoma cytotoxic T lymphocytes from healthy donors after presentation of melanoma–associated antigen–derived epitopes by dendritic cells in vitro", Cancer Res., 55(22):5330–5334 (Nov. 15, 1995).
Boehmelt, G., et al., "Dendritic cell progenitor is transformed by a conditional v–Rel estrogen receptor fusion protein v–RelER''" Cell, 80(2):341–352 (Jan. 27, 1995).
Chen, B. P., et al., "Cytokine–mobilized peripheral blood CD34+Thy–1+Lin– human hematopoietic stem cells as target cells for transplantation–based gene therapy", Leukemia, 9 Suppl 1:S17–S25 (10/95).
Conry, R.M., et al., "Selected strategies to augment polynucleotide immunization", Gene Therapy, 3(1):67–74 (1/96).
Heemskerk, M.H., et al., "Melanoma–specific CTL, generated in vitro using dendritic antigens", (Meeting abstract), Gene Therapy of Cancer: 2nd European Conference, Sep. 7–8, 1995, London, A13, XP000675471.
Reeves, Mark E., et al., "Retroviral transduction of human dendritic cells with a tumor–associated antigen gene", Cancer Res., 56(24):5672–5677 (Dec. 15, 1996).
Rouse, R.J., et al., "Induction in vitro of primary cytotoxic T–lymphocyte responses with DAN encoding herpes simplex virus proteins", J. Virol., 68(9):5685–5689 (9/94).

* cited by examiner

Primary Examiner—Anne M. Wehbe'
(74) Attorney, Agent, or Firm—Townsend and Townsend and Crew, LLP

(57) ABSTRACT

Recombinant dendritic cells are made by transforming a stem cell and differentiating the stem cell into a dendritic cell. The resulting dendritic cell is an antigen presenting cell which activates T cells against MHC class I–antigen targets. Kits, assays and therapeutics are based upon the activation of T cells by the recombinant dendritic cell. Cancer, viral infections and parasitic infections are all ameliorated by the recombinant dendritic cells, or corresponding activated T cells. Therapeutic compositions and pharmaceutical compositions are provided.

37 Claims, 6 Drawing Sheets

```
  1  TNAGGATGTC  GTCAAGAAGA  AGNGCCAGGT  TTCCGGGCCT  CACATTGNCA  NAAGACGGGA  ATATGGTGGA   70
 71  AAATAACATA  TAGACAAACG  CACACCGGCC  TTATTCCAAG  CGGNTTCGGC  CAGTAACGTT  AGGGGGGGGG  140
141  GGGAATTGAT  CCCGCTCGAA  CTGCTAGCGG  ACCTACTAAA  ATTTTAACAC  TGACTTATTA  TTAGAGATGG  210
211  NTTGNATTTT  TCCTACACCA  TTCCAAAGGA  GAACATTAGA  TGTCTGTATT  AAATTCAAGC  AAAAGTGTGA  280
281  GAGAAATAAT  TTCAGCATGT  CTCAGGTGTC  TCGCTGGCTC  TTAAGGTGAA  TAAGGTGGTG  GTGACTGTTC  350
351  TGCAGAGAGT  TTCTCATAAG  CAGGTGGAGC  ATTGGGAACA  CAGGTTCACA  GNTTTTCTCT  TGAAGAGACA  420
421  CTTTGNTGTC  CCNATGATCA  AACCCTTCTT  GTGGGCATCT  TCTTGTTAAG  GCACATTGAG  TGNCACATGA  490
491  AGACTTTTAT  CCATCAAGGG  TCTGTATCCA  TTCGGCTTCT  TCAATACCAC  AGCCCATGAG  CAGGAAGATC  560
561  CAGGNCACTG  TCAAGATGCC  GTCCCNGNGG  GCTCTCCANC  NNNGNGTAAG  AGTGCCCNGC  CCCTCTTGGG  630
631  GNACCATGGT  GAAGGGAGAT  TTCTCTTNGA  TNTNTGGGGC  AAAGGANAAG  AAACCCCCTN  ATANAGNCCC  700
701  TTCTTTTNNC  GGATGGGAAT  NGCCCCCGNT  GNCCCCCGAG  TCGTGGGGCC  NCNAANNTNG  AGGTTGGCCC  770
771  CCCCCGGGTG  GGAAGCTNCA  CNTNGGGGGG  NNTTCCCCN                                      840
```

METHODS AND COMPOSITIONS FOR TRANSFORMING DENDRITIC CELLS AND ACTIVATING T CELLS

CROSS REFERENCE TO RELATED APPLICATIONS

This application is a continuation-in-part of Provisional U.S. application U.S. Ser. No. 60/011,433 filed Feb. 8, 1996. This application claims priority to U.S. Ser. No. 60/011,433, filed Feb. 8, 1996.

BACKGROUND OF THE INVENTION

T cells mediate most forms of cellular immunity, including cell lympholysis, delayed type hypersensitivity (DTH), transplantation rejection, and allograft rejection. An introduction to T cells and cell mediated immunity is found in Paul (1993) *Fundamental Immunology, Third Edition* Raven Press, New York, N.Y. and the references cited therein.

Typical T cells do not respond to free antigenic peptides. Instead, T cells interact with a specialized set of cell surface proteins (the class I and class II major histocompatibility complexes, or MHC) which present antigens on the surface of cells. Cytotoxic T cells are induced to proliferate by specialized antigen presenting cells such as macrophage and dendritic cells which present antigenic peptides on their cellular surfaces in conjunction with MHC molecules. T cells are induced by these antigen presenting cells to recognize corresponding antigens expressed on MHC antigens on the surface of target cells. T cells destroy these target cells.

The T cell recognizes the antigen in the form of a polypeptide fragment bound to the MHC class I molecules on target cells, rather than the intact polypeptide itself. The polypeptide is endogenously synthesized by the cell, and a portion of the polypeptide is degraded into small peptide fragments in the cytoplasm. Some of these small peptides translocate into a pre-Golgi compartment and interact with class I heavy chains to facilitate proper folding and association with the subunit $\beta 2$ microglobulin. The peptide-MHC class I complex is then routed to the cell surface for expression and potential recognition by specific T cells. Investigations of the crystal structure of the human MHC class I molecule HLA-A2.1 indicate that a peptide binding groove is created by the folding of the $\alpha 1$ and $\alpha 2$ domains of the class I heavy chain (Bjorkman et al., (1987) *Nature* 329:506. Falk et al., (1991) *Nature* 351:290 have developed an approach to characterize naturally processed peptides bound to class I molecules. Other investigators have successfully achieved direct amino acid sequencing of the more abundant antigenic peptides in various HPLC fractions by conventional automated sequencing of peptides eluted from class I molecules (Jardetzky, et al. (1991) *Nature* 353:326 and mass spectrometry Hunt, et al., *Science* 225:1261 (1992). A review of the characterization of naturally processed peptides in MHC Class I is found in Rotzschke and Falk (1991) *Immunol. Today* 12:447.

Target T cells recognizing antigenic peptides can be induced to differentiate and proliferate in response to antigen presenting cells bearing antigenic peptides in the context of MHC class I and class II complexes. There are differences in the antigenic peptides bound to MHC class I and class II molecules, but the two classes of bound peptides share common epitopes within the same protein which enable a T cell activated by an antigen presenting cell to recognize a corresponding MHC class I epitope. MHC class I molecules on target cells typically bind 9 amino acid antigenic peptides, while corresponding MHC class II-peptide complexes have greater heterogeneity in the size of the bound antigenic peptide.

The generation of target T cells with a desired specificity has been limited by the ability of investigators to discover appropriate peptides for loading onto MHC molecules, and by investigator's ability to load peptide antigens onto antigen presenting cells used to induce proliferation of the T cells. In the past, investigators have generated antigen presenting cells by stripping the antigenic peptides normally found on antigen presenting cells by chemical or thermal techniques, followed by a reloading of the cells with a desired antigenic peptide. This approach has had limited success, due to inefficiencies in antigen presenting cell peptide loading, and due to the limited length of time that the loaded antigenic peptides remain loaded on the antigen presenting cells. In addition, only a single peptide fragment of a protein is loaded onto the surface of the antigen presenting cell using typical methods; thus, peptides important for activation of T cells against a target cell can be overlooked. The present invention overcomes these and other problems.

SUMMARY OF THE INVENTION

The invention provides new methods of making recombinant antigen presenting dendritic cells (DCs), which have been very difficult to transduce using existing methods. These new methods are applicable to the transduction of DCs with any recombinant nucleic acid. Also provided are new ways of expressing antigenic peptides on MHC molecules on the surface of the dendritic cells. It was surprisingly discovered that these expressed antigenic peptides are processed and displayed on the surface of the dendritic cells in the context of class I and class II MHC. These recombinant cells expressing antigenic peptides were found to be competent to activate T-cells against target cells expressing selected antigens in vivo. This provides powerful new treatments for cancers and cellular infections, as well as a variety of diagnostic and cell screening assays.

Naturally occurring dendritic cells are antigen presenting cells which activate T cell proliferation against target cells. Target cells express antigenic peptides in the context of MHC class I molecules on the surface of the target cell. Dendritic cells express related antigenic peptides on class I and class II MHC molecules. In a preferred use of the invention, dendritic cells are transformed with a nucleic acid encoding a heterologous protein which has a peptide subsequence corresponding to an antigenic peptide expressed on the surface of a target cell (on an MHC class I receptor). Preferably, a full-length protein is expressed, and several processed subsequences subsequently presented by the dendritic cell.

Surprisingly, heterologous proteins are expressed in the dendritic cell, processed into fragments, and expressed on the surface of the dendritic cell in the context of MHC class I and II molecules, making the dendritic cells capable of activating T cell proliferation against a target cell expressing the corresponding antigen. It is further demonstrated herein that T-cells activated by the dendritic cells of the invention by the methods of the invention are effective against established tumors and metastasis, in vivo. Thus, the present invention provides powerful new anti-cancer therapies based upon immunizing a patient with a recombinant dendritic cell, and/or T cell activated by a recombinant dendritic cell.

The new methods of transforming dendritic cells and expressing antigenic peptides on the surface of the cell to make the dendritic cell competent for T cell activation, provide significant advantages over prior art methods of loading peptides onto dendritic cells, including broader antigen expression and more efficient MHC class I and class II peptide loading, and the ability to expand the population of desired DCs, e.g., in culture. The invention has diagnostic, therapeutic and drug discovery assay uses.

DCs can be transduced with essentially any nucleic acid using the techniques provided. In one preferred embodiment, nucleic acids encoding cytokines (e.g., GM-CSF, an interleukin (IL-1, IL-2, IL-3, IL-4, IL-5, IL-6, IL-7, IL-8, IL-9, IL-10, IL-11, IL-12, IL-13, etc.), or cell receptor ligands (e.g., transferrin, c-kit, viral receptor ligands, cytokine receptors, and the like) are transduced into stem cells to produce recombinant DC.

In one class of embodiments, the invention provides methods of transducing dendritic cells with selected nucleic acids. In the methods, a hematopoietic stem cell, e.g., a human CD34+ stem cell, is transduced with a selected nucleic acid, and the stem cell is then differentiated into a dendritic cell. Typically, the stem cell is differentiated in vitro using appropriate cytokines. For instance, mouse stem cells are differentiated into dendritic cells by incubating the stem cells in culture with murine GM-CSF. Typically, the concentration of GM-CSF in culture is at least about 0.2 ng/ml, and preferably at least about 1 ng/ml. Often the range will be between about 20 ng/ml and 200 ng/ml. In many preferred embodiments, the dose will be about 100 ng/ml. When human cells are transduced, human GM-CSF is used in similar ranges, and TNF-α is also added to facilitate differentiation. TNF-α is also typically added in about the same ranges. Optionally, SCF is added in similar dose ranges to make human DCs. Optionally, IL-4 is added in similar ranges, particularly for making murine DCs.

Ordinarily, the differentiation process is performed in vitro. Other cytokines such as IL-4 are optionally added to facilitate cell culture and cell differentiation. In addition, lipofectamine, or a similar transduction facilitating agent, is optionally added for improving gene transfer to cultures for producing recombinant DCs.

One preferred way of transducing a hematopoietic stem cell with a selected nucleic acid is to incubate the stem cell with a retroviral vector comprising the selected nucleic acid. Preferred vectors for stem cells include murine leukemia virus vectors. For human stem cells, murine leukemia virus vectors expressing Gibbon Ape leukemia virus envelopes are also preferred. For transducing murine stem cells, ecotropic envelopes are preferred.

Thus, the invention also provides recombinant dendritic cells with expression cassettes. The expression cassettes express proteins (or peptide fragments thereof) which are processed into antigenic peptides expressed on the surface of the dendritic MHC class I and II surface receptors. The expression cassettes typically comprise a strong promoter such as a t-RNA pol III promoter, or a pol II promoter with strong constitutive expression. One preferred pol II promoter is the retroviral murine leukemia virus LTR promoter. Example antigenic proteins expressed by the expression cassette include HER-2, MART-1, gp-100 and CEA, tyrosinase, MAGE, trp-1 and PSA.

In another preferred class of embodiments, the invention provides methods for activating T cells. In the methods, the T cell is contacted with a recombinant dendritic cell expressing a recombinant protein which is processed into antigenic peptides on the surface of the dendritic cell. The T cell is optionally contacted with the dendritic cell in vitro or in vivo. Thus, in one preferred embodiment, T cells are isolated from a mammal and incubated with recombinant dendritic cells in vitro. After incubation, the T cells can be used in assays, or re-introduced into the mammal to target and kill cells with antigenic peptides (bound to class I MHC molecules) corresponding to the peptides expressed on the surface of the dendritic cell. In another preferred embodiment, the recombinant dendritic cell is introduced into a mammal to activate the T cell in vivo. Preferred target cells are those expressing antigenic peptides in the context of MHC class I molecules, including cancer cells (e.g., prostate, colon, melanoma, and breast cancer cells), virally infected cells such as cells infected with an HIV, hepatitis or herpes virus, and parasitized cells including cells with intracellular bacterial infections and cells infected with parasites such as stages of *P. falciparum* (the primary causative agent for malaria).

The invention provides commercially valuable drug and cell assays. For instance, methods for detecting T cell mediated anti-cancer cell activity of a protein or peptide are provided. In the assays, a dendritic cell is transformed with a recombinant expression cassette encoding a heterologous protein or fragment thereof (e.g., an antigenic peptide) by the methods described herein. The T cell is contacted with the dendritic cell in vivo or in vitro, thereby activating the T cell against cells expressing a peptide antigen (on a MHC class I molecule) corresponding to an antigen expressed on the surface of the dendritic cell. To test whether the T cell has anti-cancer cell activity, a selected cancer cell (for instance a breast cancer, melanoma, prostate cancer, or colon cancer cell) is incubated with the T-cell (in vitro or in vivo) and inhibition of cancer cell replication, or T-cell mediated cancer cell lysis, or specific cytokine release (e.g., GM-CSF, IFN-γ or TNF-α) is observed. The assay is optionally performed in vitro, or optionally in vivo. By providing a way of discriminating proteins which can be targeted on cancer cells, the invention provides a commercially valuable assay. The same strategy can be applied to detect antigens or virally or parasitically infected cells by substitution of these cells for the cancer cells in the assay.

The activated T cells of the invention are generally cytotoxic against cells expressing antigenic peptides in the context of MHC which correspond to antigens expressed on antigen presenting cells. Thus, the invention provides a method for making T cells cytotoxic to selected target cells. In the methods, T cells are activated by contact with the recombinant dendritic cells of the invention, in vitro or in vivo.

The transformation of dendritic cells with target proteins changes the antigenic repertoire of the dendritic cell by causing processed peptide fragments to be expressed on the MHC molecules of the dendritic cell. Unlike untransformed dendritic cells, the recombinant transformed dendritic cells have processed peptide fragments derived from the target protein expressed on the surface of the dendritic cell.

In one embodiment, diagnostic assays are provided. These assays are used to determine whether a cell population (e.g., a blood or cell sample from a patient) express a selected antigen. In the assays, recombinant dendritic cells expressing the selected antigen are used to activate T-cells against the antigen. The cell population is then exposed to the activated T-cells, and lysis of the cells is monitored (e.g., by Trypan blue exclusion). If the observed lysis is higher than an appropriate control, the population of cells comprises the antigen. This can be used, e.g., to assess whether tumor cells express a particular antigen. In another class of diagnostic assays, the invention provides a way of monitoring precursor frequency and/or T-cell reactivity by exposure to recombinant DCs. This is an indicator of the effect of immunization with DCs.

DESCRIPTION OF THE DRAWING

FIG. 3 shows the sequence of a MART-1 nucleic acid (SEQ ID NO:1).

DEFINITIONS

Figure 1:
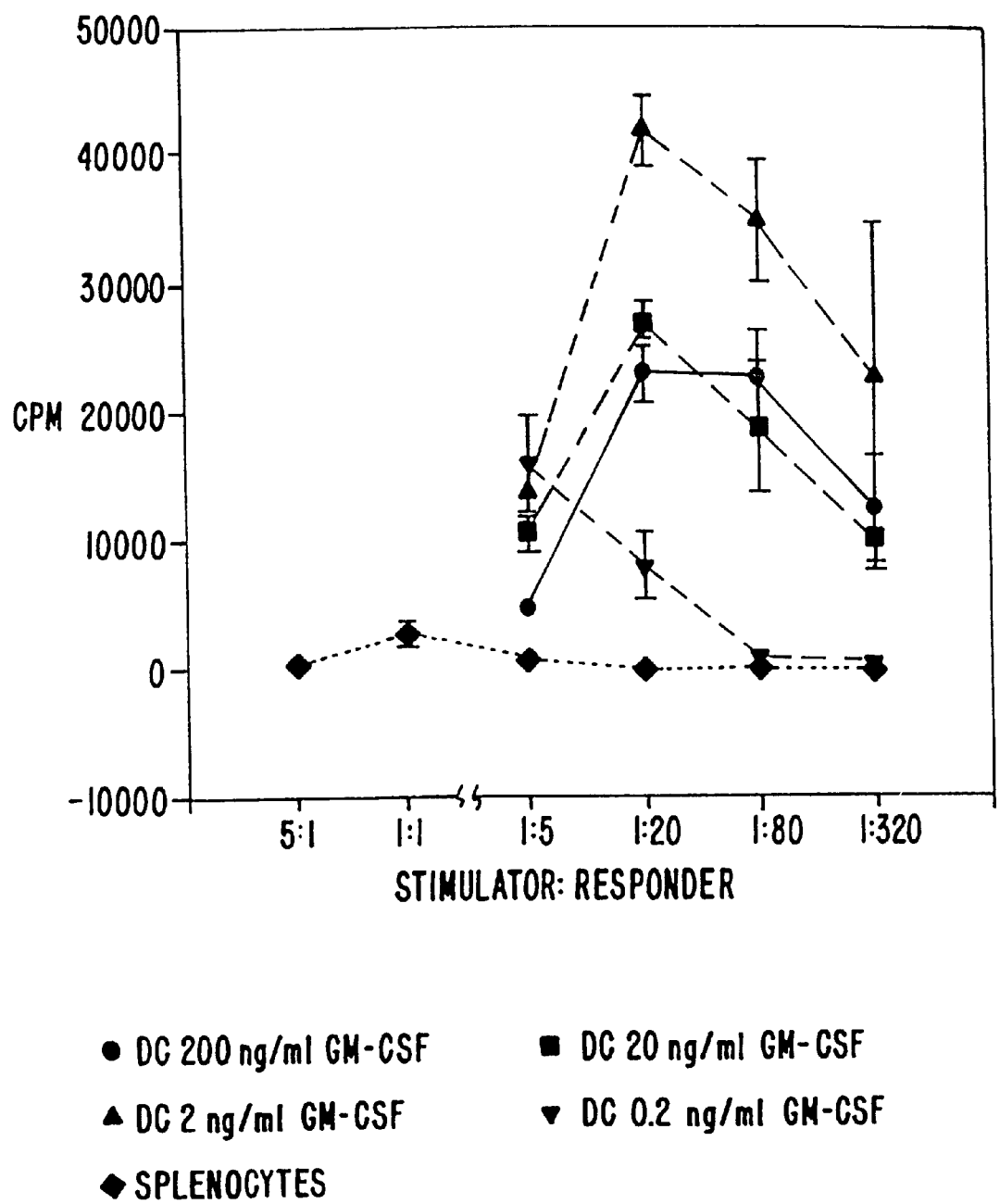
FIG. 1 shows the results of a mixed leukocyte reaction using dendritic cells to activate T cells, with Splenocytes as a control. The dendritic cells were generated with varying amounts of murine GM-CSF.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology* Harper Perennial, NY provide one of skill with a general reference for many of the terms used in this invention. Paul (1993) *Fundamental Immunology, Third Edition* Raven Press, New York, N.Y. and the references cited therein provide one of skill with a general overview of the ordinary meaning of many of the immunologically related terms herein. Although any methods and materials similar or equivalent to those described herein can be used in the practice or testing of the present invention, preferred methods and materials are described. For purposes of the present invention, the following terms are defined below.

A "dendritic cell" (DC) is an antigen presenting cell (APC) which can be derived from a hematopoietic stem cell. DC can be obtained from many lymphoid and non lymphoid tissues, as well as peripheral blood and bone marrow. Hematopoietic stem cells such as $CD34^+$ cells in humans can be artificially differentiated into DC in vitro. The dendritic cell has a characteristic morphology with thin sheets (lamellipodia) extending from the dendritic cell body in several directions. Several phenotypic criteria are also typical, but can vary depending on the source of the dendritic cell. These include high levels of MHC molecules and costimulatory molecules (e.g., B7-1 and B7-2), a lack of markers specific for granulocytes, NK cells, B cells, and T cells. In the mouse, some (but not all) dendritic cells express 33D1 (DC from spleen and Peyer's patch, but not skin or thymic medulla), NLDC145 (DC in skin and T-dependent regions of several lymphoid organs and CD11C (Cd11c also reacts with macrophage). Dendritic cells are able to initiate primary T cell responses in vitro and in vivo. These responses are antigen specific. Dendritic cells direct a strong mixed leukocyte reaction (MLR) compared to peripheral blood leukocytes, splenocytes, B cells and monocytes.

A "target cell" or a "T cell targeted cell" is a cell which expresses an antigenic peptide on a MHC class I molecule on the surface of the cell. T cells recognize the antigenic peptides bound to the MHC molecule and kill the target cell, either by cell lysis, or by recruiting other immune cells to the site of the target cell by releasing cytokines. The T cells which recognize the antigenic peptide-MHC molecule are induced to proliferate in response to antigen presenting cells (e.g., dendritic cells) which express corresponding antigenic peptides on their cell-surface MHC molecules.

A "target protein" is a protein which comprises antigenic peptide subsequences. These subsequences are expressed on target cells in the context of MHC molecules. T cells recognize epitopes formed by the binding of an MHC molecule to these peptide subsequences and typically lyse the cell, or recruit other immune cells (e.g., macrophage) to the site of the target cell, thereby killing the target cell.

An "immunogenic peptide" or "antigenic peptide" is a peptide which will bind an MHC allele to form an epitope recognized by a T cell, thereby inducing a CTL response upon presentation to the T cell. Thus, antigenic peptides are capable of binding to an appropriate MHC molecule and inducing a cytotoxic T cell response, e.g., cell lysis or specific cytokine release against the target cell which binds or expresses the antigen. The antigenic peptide can be bound in the context of a class I or class II MHC molecule, on an antigen presenting cell, or on a target cell.

"Changing the antigenic repertoire" of an antigen presenting cell such as a dendritic cell refers to the processing and expression of a heterologous protein into heterologous antigenic peptides on the surface of the antigen presenting dendritic cell (i.e., due to transformation of the antigen presenting cell with a recombinant expression cassette encoding an antigenic protein). The antigen presenting cell expresses antigenic processed fragments of the heterologous protein on the surface of the cell in the context of class I and class II MHC molecules. The expression of these heterologous processed fragments makes the antigen presenting cell competent to induce quiescent T cells which recognize the MHC-antigenic peptide epitope to proliferate against target cells which have epitopes derived from the heterologous protein (i.e., antigenic peptides expressed on MHC class I molecules on the cell). These T cells then lyse the target cells, or recruit other immune cells to the site of the target cell (e.g., macrophage) which kill the target cells.

A "hematopoietic stem cell" is a pluripotent cell found, e.g., in bone marrow or peripheral blood which can be differentiated into a given cell type by incubation in vitro or in vivo with appropriate cytokines. For instance, hematopoietic stem cells from mouse bone marrow can be differentiated into dendritic cells by incubation with murine GM-CSF, and optionally, other cytokines as shown herein. One well-characterized class of hematopoietic stem cells from humans is a class of cells which are $CD34^+$, which can be differentiated into dendritic cells by incubation with human GM CSF and TNF-α.

A cell is "transduced" with a selected nucleic acid when the nucleic acid is translocated into the cell. A cell is "stably transduced" with a selected nucleic acid when the selected nucleic acid is replicated and passed on to progeny cells. A cell is "transformed" with a selected nucleic acid when the selected nucleic acid is integrated into the cell's genome.

CD34+ cells express CD34 receptor molecules on the surface of the cell.

A cell is "negative" for a class of MHC molecules when the level of expression of the class of MHC molecules on the surface of the cell is less than 10% the level on a differentiated dendritic cell. Alternatively, a cell is "negative" for a class of MHC molecules when the cell cannot be isolated from a population of cells by FACS using the MHC molecule as a marker, or when an isotype matched antibody control binds to the cell with the same intensity (± about 5%) as an MHC antibody.

A "cell receptor ligand" is a biological molecule which binds to a cell receptor (which is optionally an extracellular receptor or an intracellular receptor), thereby activating the receptor.

The terms "isolated" or "biologically pure" refer to material which is substantially or essentially free from components which normally accompany it as found in its naturally occurring environment. The isolated material optionally comprises material not found with the material in its natural environment.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof. A nucleic acid "encodes" another nucleic acid where it is the same as the specified nucleic acid, or complementary to the specified nucleic acid.

The term "operably linked" refers to functional linkage between a nucleic acid expression control sequence (such as a promoter, or array of transcription factor binding sites) and a second nucleic acid sequence (such as a nucleic acid for a heterologous protein), wherein the expression control sequence directs transcription of the nucleic acid corresponding to the second sequence.

"Optimal differentiation" of a population of stem cells into a population of dendritic cells in the context of a titration experiment for a particular cytokine refers to achieving the highest percentage of dendritic cells in the population after incubation with the cytokine. Typically, titrations include systematically varying cytokine concentration and/or incubation time and comparing the results of the different concentrations or incubations.

An "expression vector" includes a recombinant expression cassette which has a nucleic acid which encodes a polypeptide (i.e., a protein) that can be transcribed and translated by a cell. A "recombinant expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter. In some embodiments, the expression cassette also includes, e.g., an origin of replication, and/or chromosome integration elements such as retroviral LTRs. A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also optionally includes distal enhancer or repressor elements which can be located as much as several thousand base pairs from the start site of transcription. A "constitutive" promoter is a promoter which is active under most environmental conditions and states of development or cell differentiation. An "inducible" promoter responds to an extracellular stimulus.

The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences derived from unrelated genes arranged to make a new functional nucleic acid. For example, in one embodiment, the nucleic acid has a promoter from one gene arranged to direct the expression of a coding sequence from a different gene. When used with reference to a protein, the term "heterologous" means that the protein is expressed in a cell or location where it is not ordinarily expressed in nature, such as in a recombinant dendritic cell which encodes the protein in an expression cassette.

The term "subsequence" in the context of a particular nucleic acid or polypeptide sequence refers to a region of the nucleic acid or polypeptide equal to or smaller than the particular nucleic acid or polypeptide.

A "primary" stem cell is a stem cell isolated from a patient. A "primary dendritic cell" is a dendritic cell taken from a patient, or derived by differentiation of a stem cell taken from a patient. A primary dendritic cell in an established cell culture which has undergone many serial passages in culture is not a primary dendritic cell, but may be referred to as an established dendritic cell. A "primary cultured dendritic cell" is a dendritic cell differentiated from a culture of primary stem cells.

DETAILED DISCUSSION OF THE INVENTION

Dendritic cells (DC) are highly potent antigen presenting cells that are capable of activating quiescent T-cells, and stimulate effective anti-tumor immune responses. Dendritic cells have been effective against established tumors. Dendritic cells have several advantages over other forms of anti-tumor immunization, such as recombinant viral vaccines, in that the immunization method is entirely autologous, and therefore no problems with pre-existing neutralizing antibodies are expected, even with repeated dosing. In addition, dendritic cell immunizations can be used in combination with other methods of immunization.

The ability to constitutively express tumor antigen genes in dendritic cells, as taught herein, is a powerful method to uncover new tumor antigens in vitro and to actively immunize against cells expressing the antigens in vivo and ex vivo. Methods allowing efficient gene transfer into primary dendritic cells are useful for several reasons.

First, entire antigen genes can be introduced, allowing presentation of the entire protein by the dendritic cell. Second, by permanently and stably expressing the antigen gene in dendritic cells, the antigen is constitutively expressed, compared to only transient expression with more traditional peptide pulsing. Third, introduction of the entire protein allows the presentation of multiple, and even undefined, but important, epitopes. In addition, both class I and class II epitopes can be presented. Fourth, introduction of candidate tumor antigen genes or cDNA libraries allows the identification of novel tumor antigens against common cancers. Fifth, cytokine genes, such as GM-CSF can be introduced into dendritic cells, to potentially enhance their survival, immunogenicity or therapeutic effect. Sixth, Stimulatory ligands, such as CD40L, can be introduced in dendritic cells, to enhance their survival, immunogenicity or therapeutic effects. Seventh, transcription factors and other molecules important for dendritic cell differentiation are introduced to study the basic science of primary dendritic cell development.

The invention provides new methods of transforming antigen presenting dendritic cells. In a preferred use of the invention, the dendritic cells are transformed with a nucleic acid encoding a protein which has peptide subsequences expressed on the surface of target cells in the context of MHC class I molecules. The protein is expressed in the dendritic cell, processed into fragments, and expressed on the surface of the dendritic cell in the context of the MHC class I and class II receptors found on the surface of dendritic cells. These dendritic cells are capable of activating T cell proliferation of T cells cytotoxic to a target cell.

Typically, the dendritic cells of the invention are transformed by transforming a hematopoietic stem cell with a selected nucleic acid, followed by differentiation of the stem cell into the dendritic cell. A primary advantage of this strategy is that many known methods of transducing cells require the cell to be actively dividing for stable integration of the selected nucleic acid into the cellular genome. For instance, many retroviral gene therapy vectors can only transform actively dividing cells. It is now discovered that these methods of transducing and transforming cells do not work with dendritic cells. Thus, stem cells are transformed with selected nucleic acids in the methods of the invention, and then differentiated into dendritic cells which then stably express the selected nucleic acid.

The new methods of transforming dendritic cells and expressing antigenic peptides on the surface of the cell to make the dendritic cell competent for T cell activation provides significant advantages over prior art methods of loading peptides onto dendritic cells, including broader antigen expression and more efficient MHC class I and class II peptide loading. Peptide loading methods are of limited efficiency, and ordinarily only a single peptide is loaded. In contrast, it is shown herein that endogenous expression of a protein provides for efficient loading of MHC class I and class II molecules, and that a whole range of peptides derived from a selected target protein are presented on the surface of the dendritic cell for antigen presentation. These fundamental discoveries provide diagnostic, therapeutic and assay uses.

Epitopes from a variety of pathogens on a number of potential target cells are known to mediate T cell cytotoxicity of the target cells, and it is expected that one of skill is thoroughly familiar with the identity of many such antigens. T cells recognizing such epitopes are stimulated to proliferate in response to antigen presenting cells such as dendritic cells. Examples of MHC class I bound antigens include prostate specific antigen (PSA), hepatitis B core and surface antigens (HBVc, HBVs) hepatitis C antigens, Epstein-Barr virus antigens, melanoma antigens (e.g., MAGE-1, MART-1 and gp 100), Colon cancer antigens (e.g., CEA), breast cancer antigens (e.g., HER-2) human immunodeficiency virus (HIV) antigens, herpes virus antigens, hepatitis (e.g., A, B, or C) tyrosinase, trp-1, Malarial antigens, or human papilloma virus (HPV) antigens. A nucleic acid encoding MART-1 is provided in FIG. 3.

DC can be transduced with essentially any nucleic acid using the techniques provided. In one preferred embodiment, nucleic acids encoding cytokines (e.g., GM-CSF, an interleukin (IL-1, IL-2, IL-3, IL-4, IL-5, IL-6, IL-7, IL-8, IL-9, IL-10, IL-11, IL-12, IL-13, etc.), or cell receptor ligands (e.g., transferrin, c-kit, CD40 ligand, viral receptor ligands, cytokine receptors, and the like) are transduced into stem cells to produce recombinant DC expressing the encoded protein or peptide. Cytokines and cytokine receptors, such as interleukins and interleukin receptors, c kit and the c kit receptor (see, Schwartzenberger et al. (1996) Blood 87: 472–478), as well as cell ligands (e.g., CD40), chemokines, as well as recombinant antibodies and cell surface molecules, and the like are known, and commercially available. Cytokines include, e.g., IL-1, IL-2, IL-4, TNFα, IL-6, interferons alpha, beta and gamma, and GM/CSF. See also, Cao et al. (1995) *Cancer Res Clin Oncol* 121(12):721–8; Dalgleish, (1994) *Gene Ther* 1(2):83–7; Suminami et al. (1995) *J Immunother Emphasis Tumor Immunol* 17(4):238–48; Abe et al. (1995) *J Cancer Res Clin Oncol* 121(9–10):587–92; Garbe and Krasagakis, (1993) *Invest Dermatol* 100(2 Suppl):239S–244S. For a review of the chemokine family, see, e.g., Lodi et al. (1994) *Science* 263: 1762–1767; Gronenborn and Clore (1991) *Protein Engineering* 4: 263–269; Miller and Kranger (1992) *Proc. Nat'l Acad. Sci. USA* 89: 2950–2954; Matsushima and Oppenheim (1989) *Cytokine* 1: 2–13; Stoeckle and Baker (1990) *New Biol.* 2: 313–323; Oppenheim et al. (1991) *Ann. Rev. Immunol.* 9: 617–648; Schall (1991) *Cytokine* 3: 165–183; and *The Cytokine Handbook* Academic Press, NY.

Nucleic acids encoding cytokines, growth factors, cell receptor ligands, etc., for increasing the survival, differentiation, selection (e.g., by transducing the cells with a selectable marker such as an antibiotic resistance gene), immunogenicity, or therapeutic effect of the cells are all preferably placed into a recombinant expression cassette and used to transduce DCs. DCs are optionally made which express a peptide on an MHC molecule, and simultaneously express a cytokine and/or other gene.

In preferred embodiments, primary stem cells are differentiated into dendritic cells. One of skill will appreciate that many therapeutic applications are improved by administering autologous cells to a patient, i.e., cells which were originally isolated from the patient, or which are derived from a patient by culturing isolated cells. These autologous cells are less likely to cause immune complications upon reintroduction into the patient. Moreover, primary isolates of dendritic cells are the most refractory to transduction by heterologous nucleic acids. Because the invention provides transformed dendritic cells derived from primary cell culture of stem cells, the invention overcomes this significant problem in the art.

Isolating Stem Cells

Stem cells are isolated for transduction and differentiation into dendritic cells in the methods of the invention. Many ways of isolating stem cells are known.

In mice, bone marrow cells are isolated, e.g., by sacrificing the mouse and cutting the leg bones with a pair of scissors. Stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and Ia$^d$ (differentiated antigen presenting cells). For an example of this protocol see, Inaba et al. (1992) *J. Exp. Med.* 176, 1693–1702.

Human CD34$^+$ cells can be obtained from a variety of sources, including cord blood, bone marrow, and mobilized peripheral blood. Purification of CD34$^+$ cells can be accomplished by antibody affinity procedures. An affinity column isolation procedure for isolating CD34$^+$ cells is described by Ho et al. (1995) *Stem Cells* 13 (suppl. 3): 100–105. See also, Brenner (1993) *Journal of Hematotherapy* 2: 7–17. Yu et al. (1995) *PNAS* 92: 699–703 describe a method of transducing CD34$^+$ cells from human fetal cord blood using retroviral vectors.

In humans, bone marrow aspirations from iliac crests are optionally performed e.g., under general anesthesia in the operating room. The bone marrow aspiration is approximately 1,000 ml in quantity and is collected from the posterior iliac bones and crests. If the total number of cells collected is < about $2 \times 10^8$/kg, a second aspiration is optionally performed, e.g., using the sternum and/or anterior iliac crests in addition to posterior crests. During the operation, two units of irradiated packed red cells are administered to replace the volume of marrow taken by the aspiration. Human hematopoietic progenitor and stem cells are characterized by the presence of a CD34 surface membrane antigen. This antigen is often used for purification. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 µg/ml. After two washes, paramagnetic microspheres (Dyna Beads, supplied by Baxter Immunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and preferably, an affinity column isolation procedure can be used which binds to CD34, or to antibodies bound to CD34 (see, the examples below).

In another highly preferred embodiment, CD34$^+$ cells are isolated from peripheral blood leukapheresis after G-CSF mobilization as described more fully in the examples below.

Transducing and Culturing Stem Cells

Several ways of transforming stem cells are known, including calcium phosphate precipitation, fusion of the recipient cells with bacterial protoplasts containing the DNA, treatment of the recipient cells with liposomes containing the DNA, DEAE dextran, receptor-mediated endocytosis, electroporation, micro-injection of the DNA directly into the cells, incubating viral vectors containing selected nucleic acids which encode polypeptides of interest with cells within the host range of the vector, calcium phosphate transfection, and many other techniques known to those of skill. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein, as well as Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Several approaches for introducing functional new genetic material into cells in vivo and ex vivo have been used. These include liposome based gene delivery (Debs and Zhu (1993) WO 93/24640; Mannino and Gould-Fogerite (1988) *Biotechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cometta et al. *Hum. Gene Ther.* 2:215 (1991)). Widely used retroviral vectors include those based upon murine leukemia virus (MuLV), gibbon ape leukemia virus (GaLV), ecotropic retroviruses, simian immuno deficiency virus (SIV), human immuno deficiency virus (HIV), and combinations thereof. See, e.g., Buchscher et al. (1992) *J. Virol.* 66(5) 2731–2739; Johann et al (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991), and Rosenburg and Fauci (1993) in *Fundamental Immunology, Third Edition* Paul (ed) Raven Press, Ltd., New York and the references therein, and Yu et al., *Gene Therapy* (1994) supra).

Retroviral Vectors

The preferred method of transforming stem cells is to incubate the cells with a viral vector, within the host range of the virus. Many such viral vectors are known, including retroviral vectors based on, e.g., HIV viruses, SIV viruses, murine retroviruses, gibbon ape leukemia virus and other viruses such as adeno associated viruses (AAVs) and adeno viruses.

Murine retroviral vectors are known in the art. The majority of the approved gene transfer trials in the United States rely on replication-defective retroviral vectors derived from murine retroviruses such as murine moloney retrovirus (referred to alternately as MoLv MoMuLv or MuLV in the art). See Miller et al. (1990) *Mol. Cell. Biol.* 10:4239; Kolberg R (1992) *J. NIH Res.* 4:43, and Cornetta et al. (1991) *Hum. Gene Ther.* 2:215. The major advantage of murine retroviral vectors for gene therapy are the high efficiency of gene transfer into certain types of replicating cells, the precise integration of the transferred genes into cellular DNA, and the lack of further spread of the sequences after gene transfer.

Murine vectors comprising Gibbon Ape Leukemia Virus envelopes are more broadly infective than Murine retroviruses such as Murine leukemia virus, and can be used to transduce many mammalian stem cells, including human stem cells. Gibbon Ape Leukemia Virus (GaLV) infects cells using the GaLV receptor, which is found on many cell types in many species. See, Johann et al., *J. Virol.* 66:1635–1640 (1992). GaLV can infect many mammalian species with the notable exception of mouse cells. The same receptor is used by simian sarcoma associated virus (SSAV), a strain of GaLV. Sommerfelt et al., *Virol.* 176:58–59 (1990).

The construction of hybrid virions having GaLV envelope proteins has been demonstrated. For instance, Wilson et al., *J. Virol.* 63:2374–2378 (1989), describe preparation of infectious hybrid virions with GaLV and human T-cell leukemia virus retroviral env glycoproteins and the gag and pol proteins of the Moloney murine leukemia virus (MoMLV). In addition, Miller et al., *J. Virol.* 65:2220–2224 (1991), describe construction of hybrid packaging cell lines that express GaLV envelope and MoMLV gag-pol proteins. Any of these vectors and methods of making retroviral clones can be applied to the present invention. GaLV Retroviral packaging cell lines can be used to provide infectious replication-defective hybrid virions for use in gene transfer in humans, hamsters, cows, cats, dogs, monkeys, chimpanzees, macaques, primates, and other species whose cells have host cell receptors for GaLV envelope proteins.

HIV-based retroviral vectors are made competent to transduce CD34$^+$ cells by pseudotyping the vector. This is done, for example, by transducing the packaging cell line used to package the vector with a nucleic acid which encodes the vesicular stomatitis virus (VSV) envelope protein, which is then expressed on the surface of the HIV vector. VSV infects CD34$^+$ cells, and pseudotype vectors expressing VSV envelope proteins are competent to transduce these cells (Naldini et al. (1996) *Science* 272:263).

Other HIV-based vector systems have been used. See, Akkina et al. (1996) *J Virol* 70:2581; Poznansky et al. (1991) *J Virol* 65:532; Parolin et al. (1994) *Journal of Virology* 68:3888; Richardson et al. (1995) *Journal of General Virology* 76:691; Buchschacher et al. (1992) *Journal of Virology* 66:2731; and Marlink et al. (1994) *Science* 265:1587.

A number of standard techniques are used to improve safety of retroviral vectors. For instance, a defective retroviral genome is introduced into the packaging cell separately from the genes encoding the core and envelope components. In this way, recombination between the genome and the core and envelope genes, which would lead to the packaging of complete viral genomes, is extremely unlikely. The resulting virions typically do not comprise the gag, pol, and env genes and are thus replication-defective. Homologous recombination, however, between the inserts can lead to the production of infectious virions. Accordingly, the packaging cells are produced by introducing the gag, pol, and env genes on at least two separate plasmids. This scheme effectively prevents homologous recombination leading to reconstruction of infectious virus because the probability of multiple, independent homologous recombination events occurring is extremely low.

Retroviral vectors can also be designed to prevent synthesis of viral proteins by the integrated defective genome. For instance, if a portion of the gag gene is included to increase packaging efficiency, a stop codon can be introduced into the gene to prevent synthesis of gag proteins. See, Miller et al., *Biotechniques* 7:982–988 (1989).

In addition, the cells used to make packaging cells do not typically possess a cell receptor for the relevant vector, and are thus not infectable by the vector. Thus, for instance, retroviral vector virions having the GaLV envelope cannot reinfect the packaging cells; thus, vector spread in the packaging cells is greatly reduced. Suitable packaging cells also have limited or no endogenous viral sequences. Cell lines for this purpose include the *Mus dunni* tail fibroblast cell line. This strategy decreases the potential for generation of recombinant vectors, which are often transmitted with higher efficiency than the parental vector.

Alternatively, genes are expressed in dendritic cells using recombinant adenoviral vectors, AAV vectors, pox viral vectors (B. Moss, "Poxvirus Expression Vectors", *Current Topics in Microbiology and Immunology*, Vol 158; 25–38, 1992) including vaccinia, fowl pox, and canary pox, recombinant influenza viral vectors (Garcia-Sastre, A., and P. Palese, "Influenza Virus Vectors", *Biologicals*, 23:171–178, 1995), or non-viral gene delivery techniques (F. Ledley, "Non-viral gene therapy", *Current Opinion in Biotechnology*, 5:626–636, 1994). Because some of these vectors do not require proliferating cells for gene transfer, dendritic cells are prepared by one of several methods available to those skilled in the art, such as preparation from peripheral blood over metrizamide gradient, culture of peripheral blood cells in GM-CSF and IL-4, and culture of CD34 cells in SCF, GM-CSF and TNF as described above.

Adeno Associated Viral Vectors

Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993) *Current Opinion in Genetic and Development* 3:74–80 and the references cited therein provides an overview of the AAV life cycle. AAV-based vectors are used to transduce cells with selected nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors.

The viral vectors above can be recombinantly combined with expression cassettes comprising selected nucleic acids (i.e. proteins or peptides to be expressed in dendritic cells) and incubated with the stem cells to achieve transduction. Alternately, expression cassettes comprising selected nucleic acids are packaged into viral particles using packaging cell lines, which are optionally incubated with the stem cell.

Adenoviruses (Ads) have many attractive properties for the transfer of genes, including relatively simple production of high titres of the virus and vectors based upon the virus, and low pathogenicity. Ads are well-characterized viruses, and have been widely used as nucleic acid vectors (reviewed in Haddada et al. (1995) in *Current Topics in Microbiology and Immunology* Doerfler and Bohm (eds) Springer-Verlag, Heidelberg Germany; and Yu et al., *Gene Therapy* (1994) 1:13–26. See also, Sharp and Wadell (1995) in *Principles and Practice of Clinical Virology*, Third Edition Zuckerman et al. (eds) John Wiley & Sons Ltd. and the references cited therein and Randrianarison-Jewtoukoff and Periicaudet (1995) *Biologicals* 23: 145–157 and the references cited therein). One well-characterized Ad packaging cell line is the 293 cell line described in Haddada et al. (1995), supra. Ads are extrachromosomal viruses which do not integrate into the genome of cells transduced by the virus.

The culture of cells used in conjunction with the present invention, including cell lines and cultured cells from tissue or blood samples, including stem cells and dendritic cells is well known in the art. Freshney (*Culture of Animal Cells, a Manual of Basic Technique, third edition* Wiley-Liss, New York (1994)) and the references cited therein provides a general guide to the culture of cells. See also, Kuchler et al. (1977) *Biochemical Methods in Cell Culture and Virology*, Kuchler, R. J., Dowden, Hutchinson and Ross, Inc, and Inaba et al., supra.

Differentiating Stem Cells into Dendritic Cells

Transduced stem cells are differentiated into dendritic cells by incubating the cells with the appropriate cytokines. Inaba et al. described the in vitro differentiation of murine stem cells into dendritic cells by incubating the stem cells with murine GM-CSF. In brief, isolated stem cells are incubated with between 1 and 200 ng/ml murine GM-CSF, and preferably about 20 ng/ml GM-CSF in standard RPMI growth medium. The media is changed with fresh media about once every other day. After 7 days in culture, a large percentage of cells are dendritic, as assessed by expression of surface markers and morphology. Dendritic cells are isolated by florescence activated cell sorting (FACS) or by other standard methods.

Human cells $CD34^+$ hematopoietic stem cells are preferably differentiated in vitro by culturing the cells with human GM-CSF and TNF-α. See, the examples and Szabolcs et al. (1995) 154: 5851–5861.

For mouse DCs, murine stem cells are differentiated into dendritic cells by incubating the stem cells in culture with murine GM-CSF. Typically, the concentration of GM-CSF in culture is at least about 0.2 ng/ml, and preferably at least about 1 ng/ml. Often the range will be between about 20 ng/ml and 200 ng/ml. In many preferred embodiments, the dose will be about 100 ng/ml. IL-4 is optionally added in similar ranges for making murine DCs.

When human cells are transduced, human GM-CSF is used in similar ranges, and TNF-α is also added to facilitate differentiation. TNF-α is also typically added in about the same ranges. Optionally, SCF or other proliferation ligand (e.g., Flt3) is added in similar dose ranges to make human DCs.

It will be appreciated that all of these dose ranges for differentiating stem cells are approximate. Different suppliers and different lots of cytokine from the same supplier vary in the activity of the cytokine. One of skill can easily titrate each cytokine which is used to determine the optimal dose for any particular cytoline. An example titration is performed in the Examples, supra.

Isolation of and Expansion of T Cells

T cells are isolated from mammals in some embodiments of the invention where the T cell is activated in vitro by contact with a dendritic cell of the invention. Several techniques are known. The expression of surface markers facilitates identification and purification of T cells. Methods of identification and isolation of T cells include FACS, incubation in flasks with fixed antibodies which bind the particular cell type and panning with magnetic beads.

In one method, Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 μg/ml gentamicin sulfate, 50 μg/ml streptomycin) supplemented with 1% fetal bovine serum FBS). Enrichment for T cells is performed by negative or positive selection with appropriate monoclonal antibodies coupled to columns or magnetic beads according to standard techniques. An aliquot of cells is analyzed for cell surface phenotype including CD4, CD8, CD3 and CD14.

Cells are washed and resuspended at a concentration of $5 \times 10^5$ cells per ml of AIM-V modified as above and containing 5% FBS and 100 U/ml recombinant IL-2 (rIL-2) (supplemented AIM-V). Where the cells are isolated from and $HIV^+$ patient, 25 nM CD4-PE40 (a recombinant protein consisting of the HIV-1-binding CD4 domain linked to the translocation and ADP-ribosylation domains of *Pseudomonas aeruginosa* exotoxin A), or other similar recombinant cytotoxic molecule which selectively hybridizes to HIV is added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells.

To stimulate proliferation, OKT3 monoclonal antibody (Ortho Diagnostics) is added to a concentration of 10 ng/ml and the cells are plated in 24 well plates with 0.5 ml per well. The cells are cultured at 37° C. in a humidified incubator with 5% $CO_2$ for 48 hours. Media is aspirated from the cells and 1 ml of vector-containing supernatant (described below) supplemented with 5 μl/ml of protamine sulfate, 100 U/ml rIL-2, 100 U/ml penicillin, 0.25 μg/ml amphotericin B/ml and an additional 100 μg/ml streptomycin (25 nM CD4-PE40 can be added as described above).

Isolating Cells with Selectable Markers

A variety of cells are used in the methods of the invention, including stem cells, T cells and dendritic cells. Each of these cell types is characterized by expression of particular markers on the surface of the cell, and lack of expression of other markers. For instance, human stem cells typically express CD34 antigen. Dendritic cells express MHC molecules and costimulatory molecules (e.g., B7-1 and B7-2), a lack of markers specific for granulocytes, NK cells, B cells, and T cells. In the mouse, some (but not all) dendritic cells express 33D1 (DC from spleen and Peyer's patch, but not skin or thymic medulla), NLDC145 (DC in skin and T-dependent regions of several lymphoid organs and CD11c (CD11c also reacts with macrophage). T cells are positive for various markers depending on the particular subtype, most notably CD4 and CD8.

The expression of surface markers facilitates identification and purification of these cells. These methods of identification and isolation include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, NY; and Harlow and Lane (1989) *Antibodies: A Laboratory Manual* Cold Spring Harbor Press, NY; Stites et al. (eds.) Basic and Clinical Immunology (4th ed.)

Cell isolation or immunoassays for detection of cells during cell purification can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Nonisotopic Immunoassays* Plenum Press, NY.

Most preferably, cells are isolated and characterized by flow cytometry methods such a FACS analysis. A wide variety of flow-cytometry methods are known. For a general overview of fluorescence activated flow cytometry see, for example, Abbas et al. (1991) *Cellular and Molecular immunology* W.B. Saunders Company, particularly chapter 3, and Kuby (1992) *Immunology* W.H. Freeman and Company, particularly chapter 6. FACS machines are available, e.g., from Becton Dickinson.

Labeling agents which can be used to label cell antigen include e.g., monoclonal antibodies, a polyclonal antibodies, proteins, or other polymers such as affinity matrices, carbohydrates or lipids. Detection proceeds by any known method, such as immunoblotting, western blot analysis, tracking of radioactive or bioluminescent markers, capillary electrophoresis, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates cell cytometry and immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., 3H, 125I, 35S, 14C, or 32P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired component of the assay according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which are used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it is optionally detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product.

Finally, simple calorimetric labels are often detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of antibodies. In this case, cells are agglutinated by samples comprising the antibodies bound to the cells. In this format, none of the components need be labeled and the presence of the target antibody is detected by simple visual inspection.

Depending upon the assay, various components, including the antibody, or anti-antibody, are typically bound to a solid surface. For instance, in one preferred embodiment, unwanted cells are panned out of bone marrow using appropriate antibodies bound to a substrate over which the cells are passed. Many methods for immobilizing biomolecules to a variety of solid surfaces are known in the art. For instance, the solid surface is optionally a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, a flask, or a glass, silica, plastic, metallic or polymer bead. The desired component is optionally covalently bound, or noncovalently attached through nonspecific bonding. A wide variety of organic and inorganic polymers, both natural and synthetic are optionally employed as the material for the solid surface. Illustrative polymers include polyethylene, polypropylene, poly(4-methylbutene), polystyrene, polymethacrylate, poly (ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable.

Diagnostic Assays

In one embodiment, diagnostic assays are provided. These assays are used to determine whether a cell population (e.g., a blood or cell sample from a patient) express a selected antigen. In the assays, recombinant dendritic cells expressing the selected antigen are used to activate T-cells against the antigen. The cell population is then exposed to the activated T-cells, and lysis of the cells is monitored (e.g., by trypan blue exclusion). If the observed lysis is higher than an appropriate control, the population of cells comprises the antigen. This can be used, e.g., to assess whether tumor cells express a particular antigen. If the tumor is found to express a particular antigen, a clinician can use the information to better select therapeutics against the tumor.

These diagnostic assays can be used in conjunction with the therapeutic aspects of the invention, i.e., a tumor sample can be screened against a panel of activated T-cells to determine which activated T-cells or recombinant DCs can be used to immunize against the tumor.

Immunizations can also be monitored with recombinant DCs. Precursor frequency and/or T-cell reactivity is monitored by exposure to recombinant DCs, e.g., using DCs corresponding to the DCs which were used for immunization or to stimulate T-cells.

Making Expression Cassettes

Many recombinant expression cassettes are known to persons of skill. These can be made using standard recombinant or synthetic techniques, and one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger, Sambrook and Ausbel (all supra). The nucleic acid compositions of this invention, whether RNA, DNA, cDNA, genomic DNA, or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro amplification techniques suitable for amplifying sequences to be subcloned into an expression vector are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook et al. (1989) *Molecular Cloning—A Laboratory Manual* (2nd Ed) Vol. 1–3; and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Nucleic acid synthesis techniques are available, such as the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Nucleic acids can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given nucleic acid sequence such as a known cancer marker. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausbel, Berger, Needham VanDevanter and Mullis (all supra).

In addition to recombinant expression, polypeptides of the invention can be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis*, 2d. ed., Pierce Chemical Co. Polypeptides are also produced by recombinant expression of a nucleic acid encoding the polypeptide followed by purification using standard techniques.

The Expression cassette used to transform the host cell preferably contains DNA sequences to initiate transcription and sequences to control the translation of any encoded antigenic protein or peptide sequence. These sequences are referred to as expression control sequences. When illustrative expression control sequences active in mammalian cells are obtained from the SV-40 promoter (*Science*, 222:524–527, 1983), the CMV I.E. Promoter (*Proc. Natl. Acad. Sci.* 81:659–663, 1984) and the metallothionein promoter (*Nature* 296:39–42, 1982). Pol III promoters such as $tRNA_{val}$, a house-keeping cellular gene promoter, and the adenovirus VA1, a strong viral promoter are also desirable. The cloning vector containing the expression control sequences is cleaved using restriction enzymes and adjusted in size as necessary or desirable and ligated with nucleic acid coding for the target polypeptides by means well known in the art.

Polyadenlyation or transcription terminator sequences from known mammalian genes are typically incorporated into the vector. Pol III termination sequences are outlined in Geiduschek, E. P., *Ann. Rev. Biochem.* 57:873–914 (1988). An example of a terminator sequence is the polyadenlyation sequence from the bovine growth hormone gene. Sequences for accurate splicing of the transcript are also be included. An example of a splicing sequence is the VP1 intron from SV40 (Sprague, J. et al., 1983, *J. Virol.* 45: 773–781).

Additionally, sequences to control replication in the host cell is optionally incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

Where a retroviral packaging vector is used, a packaging site containing the nucleic acids responsible for packaging viral RNA into the retroviral particle is included with the expression cassette. Typically, this includes nucleic acids corresponding to those from a retrovirus located between the LTR of the retrovirus and the gag initiation codon.

MLR Assays

In order to determine the antigen presenting cell activity of antigen presenting cells such as DC, the proliferative effect of these antigen presenting cells on T cells is tested in an MLR assay. MLR assays or "mixed lymphocyte response" assays are the standard in vitro assay of antigen presenting function in cellular immunity. The assay measures the proliferation of T cells after stimulation by a selected cell type. The number of T cells produced are typically characterized by measuring T cell proliferation based on incorporation of $^3$H-thymidine in culture. Similar methods are used in vivo in nude or SCID mouse models. See also, Paul (supra) at chapter 31.

Ex Vivo Therapy

Ex vivo therapeutic methods for making transformed dendritic cells and activated T cells are provided. In the methods, dendritic cells are transformed in vitro. These transformed dendritic cells are used to activate T cells in vitro, or the dendritic cells are introduced into a mammal to activate the T cell in vivo. T cells such as CD8$^+$ CTLs activated in vitro are introduced into a mammal where they are cytotoxic against target cells bearing antigenic peptides corresponding to those the T cells are activated to recognize on class I MHC molecules. These target cells are typically cancer cells, or infected cells which express unique antigenic peptides on their MHC class I surfaces. It is shown herein that dendritic cells expressing cancer antigens activate T-cells against corresponding cancers.

Similarly, helper T-cells (e.g., CD4$^+$ T cells), which recognize antigenic peptides in the context of MHC class II, are also stimulated by the recombinant DCs, which comprise antigenic peptides both in the context of class I and class II MHC. These helper T-cells also stimulate an immune response against a target cell. As with cytotoxic T-cells, helper T-cells are stimulated with the recombinant DCs in vitro or in vivo.

The dendritic cells and T cells are preferably isolated from the mammal into which the activated T cells are to be active ("autologous" therapy). Alternatively, the cells can be those from a donor or stored in a cell bank (e.g., a blood bank).

Thus, a patient infected with a virus such as HIV-1 or suffering from a cancer such as a melanoma can be treated by administering recombinant dendritic cells, or by using recombinant dendritic cells to activate a population of the patient's T cells against the infection or cancer, and introducing the T cells back into the patient as described herein. Thus, the present invention provides a method of producing cytotoxic T cells in vitro, ex vivo or in vivo.

In Vivo Therapy

T cells or dendritic cells can be administered directly to the organism to produce T cells active against a selected cancerous or infected cell type. Administration of these is by any of the routes normally used for introducing a cell into ultimate contact with a mammal's blood or tissue cells.

The cells are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Most typically, quality controls (microbiology, clonogenic assays, viability tests), are performed and the cells are reinfused back to the patient, preceded by the administration of diphenhydramine and hydrocortisone. See, for example, Korbling, M. et al. (1986) *Blood*, 67:529–532 and Haas et al. (1990) *Exp. Hematol.* 18:94–98.

Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous or intraperitoneal administration are the preferred method of administration for dendritic or T cells of the invention.

The dose of cells (e.g., activated T cells, or dendritic cells) administered to a patient, in the context of the present invention should be sufficient to effect a beneficial therapeutic response in the patient over time, or to inhibit growth of cancer cells, or to inhibit infection. Thus, cells are administered to a patient in an amount sufficient to elicit an effective CTL response to the virus or tumor antigen and/or to alleviate, reduce, cure or at least partially arrest symptoms and/or complications from the disease or infection. An amount adequate to accomplish this is defined as a "therapeutically effective dose." The dose will be determined by the activity of the T cell or dendritic cell produced and the condition of the patient, as well as the body weight or surface area of the patient to be treated. The size of the dose also will be determined by the existence, nature, and extent of any adverse side-effects that accompany the administration of a particular cell in a particular patient. In determining the effective amount of the cell to be administered in the treatment or prophylaxis of diseases such as AIDS or cancer (e.g., metastatic melanoma, prostate cancer, etc.), the physician needs to evaluate circulating plasma levels, CTL toxicity, progression of the disease, and the production of immune response against any introduced cell type.

Prior to infusion, blood samples are obtained and saved for analysis. Generally at least about $10^4$ to $10^6$ and typically, between $1\times10^8$ and $1\times10^{10}$ cells are infused intravenously or intraperitoneally into a 70 kg patient over roughly 60–120 minutes. Intravenous infusion is preferred. Vital signs and oxygen saturation by pulse oximetry are closely monitored. Blood samples are obtained 5 minutes and 1 hour following infusion and saved for analysis. Cell reinfusion are repeated roughly every month for a total of 10–12 treatments in a one year period. After the first treatment, infusions can be performed on a outpatient basis at the discretion of the clinician. If the reinfusion is given as an outpatient, the participant is monitored for at least 4 hours following the therapy.

For administration, cells of the present invention can be administered at a rate determined by the LD-50 (or other measure of toxicity) of the cell type, and the side-effects of the cell type at various concentrations, as applied to the mass and overall health of the patient. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment by the DCs or activated T cells of the invention. For example, the cells are optionally administered with an adjuvant, or cytoline such as GM-CSF, IL-12 or IL-2.

The studies presented herein demonstrate that tumor antigen genes are expressed by dendritic cells using retroviral transduction, and that these dendritic cells (and T cells activated by the dendritic cells) can be used as anti-tumor therapeutics. Transduced dendritic cells are valuable reagents for active immunization strategies against cancer and infectious diseases, and are useful in vitro to uncover unique tumor epitopes and antigens, and as a tool to study the basic biology of primary dendritic cells. Accordingly, in one specific example of the administration methods shown above, metastatic melanoma patients are immunized with autologous dendritic cells transduced with the MART-1 or GP100 tumor antigen genes to inhibit melanoma metastasis and disease progression, or, alternatively, melanoma patients are immunized with activated T cells (or both activated T-cells and dendritic cells) transduced with the MART-1 or GP100 tumor antigen genes to inhibit melanoma metastasis and disease progression, using the dosing and administration methods set forth above.

In Vitro Assays and Kits

The present invention provides commercially valuable assays and kits to practice the assays. In the assays of the invention, dendritic cells are transformed with a nucleic acid encoding a putative T cell MHC class I associated antigen. The dendritic cell is used to activate the T cell, which is then tested for cytotoxic activity against a class of target cells thought to comprise the putative antigen. Cytotoxicity indicates that the target cells comprise the antigen, and that the antigen is sufficient to mediate a T cell recognition of the target cell. This assay provides investigators with a lead molecule for use in gene therapy or vaccination therapies. Because the transformed dendritic cells can be established in culture, or made in batches, several potential target cell populations can be screened. Thus, libraries of potential tumor antigens can be screened by cloning into dendritic cells. The ability to screen and identify tumor antigens is of considerable commercial value to pharmaceutical and other drug discovery companies.

Kits based on the assay are also provided. The kits typically include a container, and stem cells or dendritic cells. The kits optionally comprise directions for performing the assays, stem cell transformation vectors, cytokines, or instructions in the use of any of these components, or the like.

EXAMPLES

The following examples are provided by way of illustration only and not by way of limitation. Those of skill will readily recognize a variety of noncritical parameters which can be changed or modified to yield essentially similar results.

Example 1

Differentiation of Bone Marrow Cells into Dendritic Cells in Vitro

Freshly isolated dendritic cells from peripheral blood are difficult to transduce, particularly with common retroviral vectors, because they are non-dividing. Accordingly, a novel approach to transforming dendritic cells was derived. Stem cells were transduced, and then differentiated into dendritic cells. The following procedure was used to differentiate bone marrow cells isolated from mice into dendritic cells in vitro.

Bone marrow was harvested from 5 BALB-C mice. To remove B cells, T cells, granulocytes, and $Ia^+$ cells, the bone marrow cells were incubated with an antibody cocktail against CD8, CD4, CD45R (pan B cell), GR-1 (granulocyte), and $Ia^d$ (all antibodies were of rat origin except anti-Ia from mouse). All antibodies were obtained from Cedar Lane (Canada). The bone marrow cells were then incubated on a mouse anti-rat flask to remove rat antibody-bound cells, followed by an incubation of the non-adherent cells in a goat anti-mouse flask to remove cells labeled with anti-mouse antibodies. As an alternative method to remove unwanted cells, rabbit complement was added at a 1:10 ratio at 37° C. following incubation with the antibodies. Non-adherent cells were then cultured in RPMI with 5% fetal calf serum containing 3.3 to 20 ng/ml mGM-CSF. Every two days, the medium was changed with fresh medium containing fresh GM-CSF, and non-adherent cells (typically granulocytes) were removed. At day 6, moderately adherent cells (dendritic cells) were removed by gentle pipetting, and replated. Adherent cells (macrophage) were left on the plate. On day 7, the dendritic cells were phenotyped by FACS analysis and microscopy, which confirmed a dendritic phenotype, and that $B7-1^+$, $B7-2^+$ and $Cd11c^+$ dendritic cells were present. Typically, $5 \times 10^6$ dendritic cells were obtained by day 7.

In one variation, GM-CSF was titrated over a range of 200, 20, 2, and 0.2 ng/ml, and the contaminating granulocytes (which are completely non adherent, as opposed to lightly adherent dendritic clumps) were removed during differentiation by performing extra washes. In addition, a procedure which substituted rat anti-$Ia^d$ antibody was used, so that only a single mouse anti-rat flask was needed.

The percent of cells in the final cultures that were dendritic cells by morphology was also affected by the level of GM-CSF, with 62% appearing dendritic at 200 ng/ml, 60% appearing dendritic at 20 ng/ml; 44% appearing dendritic at 2 ng/ml, and 6% appearing dendritic at 0.2 ng/ml. Thus, typically, at least 2 ng GM-CSF is used in culture, and preferably, at least about 20 ng/ml. The percent which showed dendritic markers by FACS were similar:

TABLE 1

Phenotypic Analysis by FACS

| Antibody | DC[1]: 200 ng/ml GM-CSF | DC: 20 ng/ml GM-CSF | DC: 2 ng/ml GM-CSF | DC: .2 ng /ml GM-CSF | Spleno-cytes |
|---|---|---|---|---|---|
| Total B7-2 | 67% | 65% | 44% | 7% | 51% |
| Total Ia$^d$ | 60% | 55% | 41% | 7% | 38% |
| Thy 1.2 | 51% | 49% | 35% | 5% | 10% |
| B7-2 and Ia$^d$ | 25% | 20% | 10% | 4% | 48% |
| Gr-1 (granulocyte) | 16% | 21% | 24% | 89% | 17% |
| B220 (B-cell) | 18% | 15% | 13% | 11% | 38% |
| Total MAC-1 | 76% | 84% | 83% | 82% | 8% |
| Total B7-1 | 54% | 48% | 29% | 8% | 1% |
| B7-1 pos/MAC neg | 8% | 5% | 3% | 0% | 1% |

[1]DC = dendritic cells.
*high background with IgG control on splenocytes

In this experiment, an MLR assay was performed as described above for each GM-CSF titration. The results are shown in FIG. 1. As seen from the results, 0.2 ng/ml GM-CSF promotes inefficient differentiation into functional dendritic cells. Thus, about 2 ng/ml or more is preferred.

Figure 2:
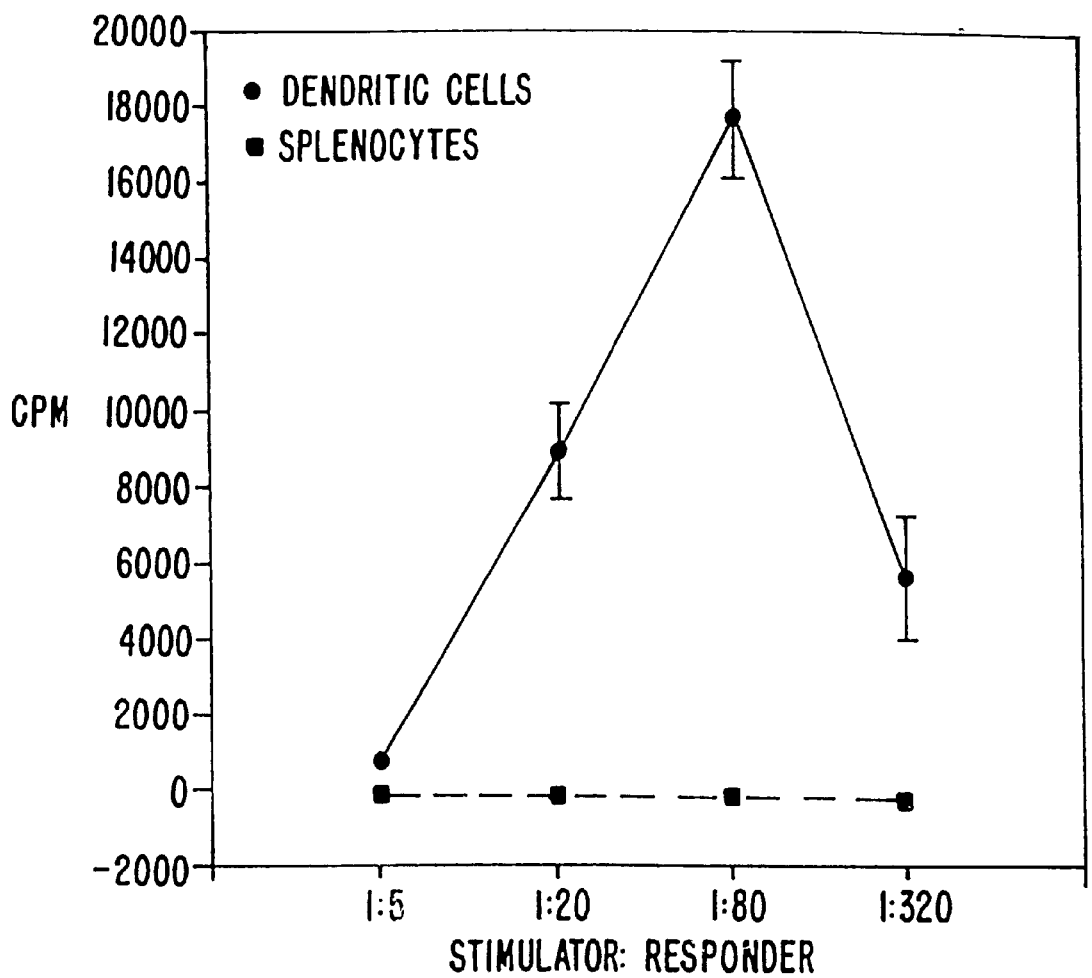
FIG. 2 shows the results of a mixed lymphocyte reaction using dendritic cells to activate T cells, with Splenocytes as a control.
Figure 4:
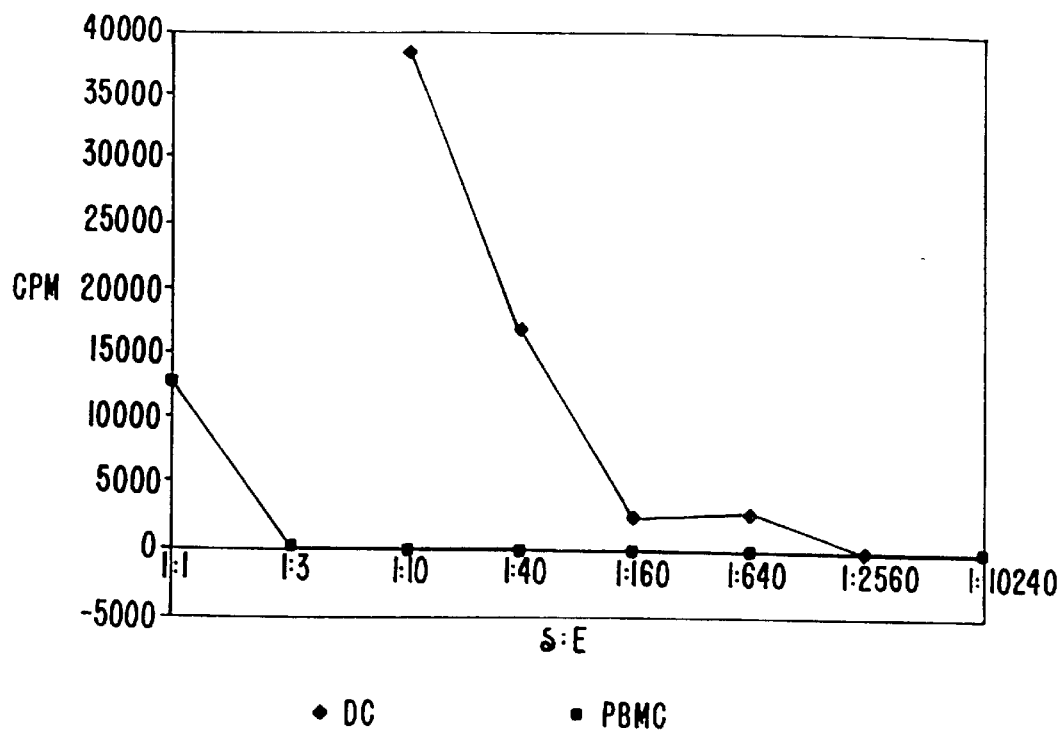
FIG. 4 shows an allogenic MLR with dendritic cells and PBMC.
Figure 5:
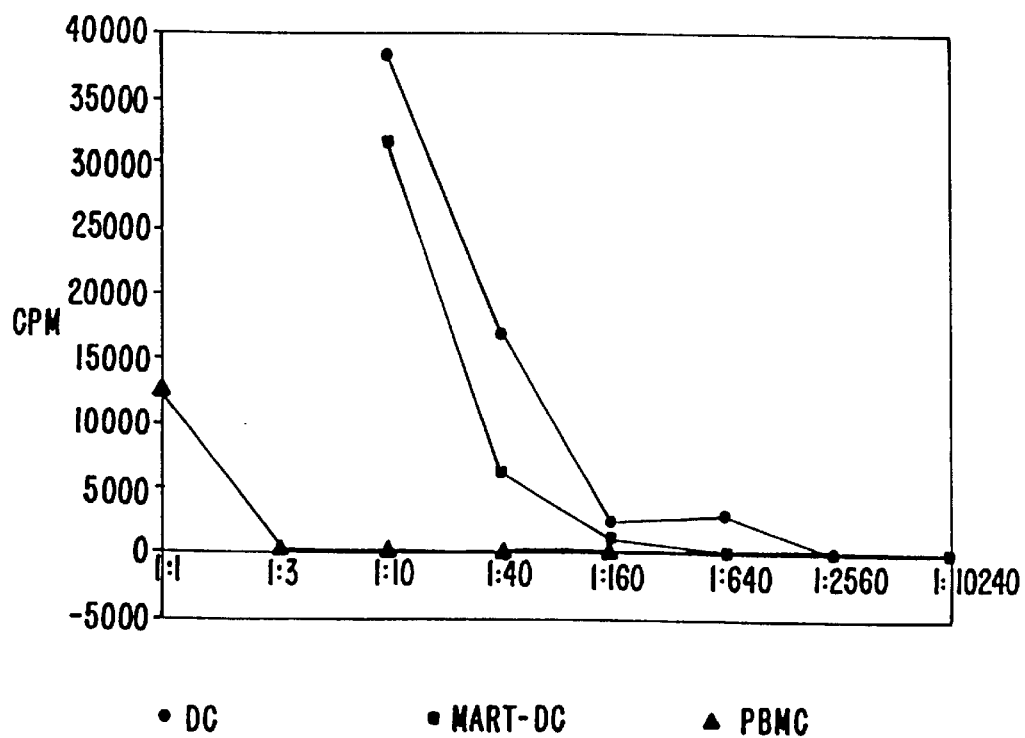
FIG. 5 shows an allogenic MLR with dendritic cells, MART transformed dendritic cells and PBMC.

To show that the dendritic cells were functional, the activity of the cells was tested in a standard mixed leukocyte reaction (MLR) assay as in Inaba et al. (1992) supra. Stimulator cells in the MLR were day 7 BALB dendritic cells vs BALB splenocytes (1500 rads). Responders were C57B1/6 splenocytes purified for T cells on an R&D systems negative selection column (MTCC-1000) using the manufacturer's directions. The column contained antibodies to remove B cells, granulocytes and macrophage. Thus, T cells pass through the column. The stimulators and responders were plated in standard 96 well plates at ratios of 1:5, 1:20, 1:80 and 1:320 using $3 \times 10^5$ responders/well. Four days after plating, the cells were pulsed with $^3$H-thymidine at 1 $\mu$Ci/well. Proliferation was then measured by monitoring thymidine uptake. The results are shown in FIG. 2 (T cell alone and dendritic cell alone values were subtracted). As the results show, the dendritic cells dramatically stimulated proliferation, while the splenocytes have no proliferative effect. Thus, the dendritic cells were functional, i.e., they induced proliferation in T-cells.

Thus, dendritic cells were cultured from murine bone marrow using GM-CSF (see also, Inaba, 1992, supra). Bone marrow-derived cells express B7-1, B7-2, Ia and Cd11c, and have characteristic dendritic morphology. Bone marrow derived dendritic cells act as antigen presenting cells, with high levels of T cell activation as measured in a standard MLR assay.

Example 2

Transduction of Bone-Marrow Derived Dendritic Cells

Primary, mature dendritic cells are difficult to gene modify using existing techniques. Accordingly, the present invention provides a new strategy for genetic modification of dendritic cells. In the methods of the invention, hematopoietic stem cells are gene modified, and differentiated into dendritic cells. It is demonstrated herein that this novel technique generated dendritic cells expressing foreign genes. MART-1 and GP100 melanoma antigens were expressed by dendritic cells, and these cells stimulated MART-1- and GP100-specific T-cells, and generated specific T-cells from resting lymphocytes. In murine tumor models, dendritic cells, gene modified with a model tumor antigen, effectively immunized against established tumors. This technique allowed the generation of specific T-cells against common tumors and provides a novel method to actively immunize patients against known tumor antigens, i.e., by utilizing dendritic cells transduced with antigen or cytokine genes, or ex vivo activated T-cells.

Murine Dendritic Cell Studies: Murine bone marrow cells were successfully transduced with a retroviral vector encoding the β-galactosidase model tumor antigen. Following in vitro differentiation into dendritic cells using GM-CSF, supplemented by IL4, 30–40% of dendritic cells were positive for β-galactosidase expression. In addition, T-cells specific for β-galactosidase expressed large amounts of cytokines such as IFN-γ when co-cultured with the transduced but not the non-transduced dendritic cells. These studies indicated that dendritic cells were transduced using these methods to express foreign genes.

In one series of experiments, 50 BALB/c mice were injected intraperitoneally with 5-fluorouracil (5FU, Sigma Chemical CO. St. Louis, Mo.) at 3 mg/mouse (150 mg/kg) (the 5FU injection is optional). After two days, bone marrow was harvested. $7 \times 10^6$ cells per mouse were obtained. Cells were co-cultured on irradiated ecotropic LZSN packaging cells (LZSN contains the β-gal gene) for two days. The vector was introduced into the GP+E86 ectropic packaging cell line. See, Miller (1989) Biotechniques 7: 980; Miller (1986) Mol. Cell Biol. 6:2895; Markowitz (1988) J. Virol. 62: 420, and Wang et al. (1995) J. Immunol. Each day, fresh ecotropic supernatant was added, followed by centrifugation for 1 hour at 1000 g. The supernatant was supplemented with polybrene and 20 ng/ml GM-CSF. On day 2, cells were harvested, and dead cells were removed with Ficoll. The live cells were replated at 20 ng/ml GM-CSF.

TABLE 2

Cytokine Release from β-gal specific T-cell Clone in Response to Murine Dendritic Cells Transduced with the β-gal Gene

| | Responder [mIFN-γ production; U/ml1 x $10^5$ T-cells/18 Hours] | |
|---|---|---|
| Stimulator | None | Beta-gal specific T-cell clone |
| None | 0 | 5 |
| DC NV | 0 | 67 |
| DC; β-gal transduced | 0 | 64,600 |

In another series of experiments, bone marrow was harvested from femur and tibia as described, supra. Lymphocytes and Ia+ cells were removed. Bone marrow cells were co-cultured on irradiated ecotropic bgal producer cells for 2 days, in the presence of murine GM-CSF, murine IL-4 and lipofectamine. Cells were harvested and replated with fresh mGM-CSF and mIL-4. On day 6, cells were harvested, pelleted, and replated in fresh media. Cells were assayed and used for therapy on day 7.

On day 7, the resulting dendritic cells were stained with X-gal. Cells that were morphologically dendritic were positive for X gal as examined by light microscopy. 38% of the cells were positive. Thus, the dendritic cells were transformed with the foreign X-gal gene which had been used to transform the hematopoietic stem cells. As shown in Table 3, co-culturing provided better transformation than supernatant transduction alone.

TABLE 3

Percent of Murine Dendritic Cells Transduced with β-gal Retrovirus

| Experiment | Nontransduced | β-gal transduced Supernatant | β-gal transduced Co-cultured |
|---|---|---|---|
| #1 | 0 | 8 | 28 |
| #2 | 0 | N.D. | 38 |

N.D. = Not Done

To demonstrate that transduced dendritic cells presented antigen, 1×10$^5$ dendritic cells were co-cultured with 1×10$^5$ H-2$^d$ T cells specific for beta gal. After 24 hours of co-culture, the supernatants were assayed for murine IFN-γ. A large amount of IFN-γ was present in the supernatant (34,650 pg/ml) upon co-culture with T cells, as compared to controls (controls had 3,561 and 6,761 pg/ml; see, Table 4).

TABLE 4

Cytokine Release from β-gal specific T cell Clone in Response to Murine Dendritic Cells Transduced with the β-gal gene

| Stimulator | Responder (mIFN-γ production; pg/ml/1 × 10$^8$ T cells/17 hours) | |
|---|---|---|
| | None | β-gal specific T cell Clone |
| none | 0 | 3561 |
| DC NV | 1 | 6671 |
| DC; β-gal transduced | 1 | 34,650 |
| CT26; β-gal transduced | 0 | 75,550 |

To study the ability of transduced dendritic cells to immunize in vivo, mice were immunized on day 0 with PBS, untranduced dendritic cells (3×10$^5$ per mouse), beta gal-transduced dendritic cells (3×10$^5$ per mouse), or irradiated lac Z (LZSN) producer cells (3×10$^5$ per mouse, to show that any producer cells which were transferred from the dendritic cell co-culture were not responsible for immunization). On day 21, mice were challenged by IV with 10$^5$ beta gal CT26 mouse tumor line cells (Wang et al. (1995) *Journal of Immunology*). These CT26 cells were beta gal positive; thus, T cells activated against CT26 tumor cells will destroy the cells.

On day 33, mice were sacrificed and lung metastases were counted. Mice immunized with beta-gal transduced dendritic cells had statistically lower numbers of metastases compared to the PBS and LZSN producer cell lines (Table 5).

TABLE 5

Immunization Followed by Challenge 21 Days Later

| Immunized with (day 0) | Challenged with (day 21) | n | mean # lung metastases |
|---|---|---|---|
| PBS | β-gal transduced CT26 | 6 | 175 |
| Dendritic Cells NV | | 5 | 61 |
| β-gal transduced DC | | 6 | 1 |
| Irradiated LZSN Producer Line | | 7 | 158 |

Example 3

Treatment of Established Pulmonary Metastases with Transduced Dendritic Cells

Figure 6:
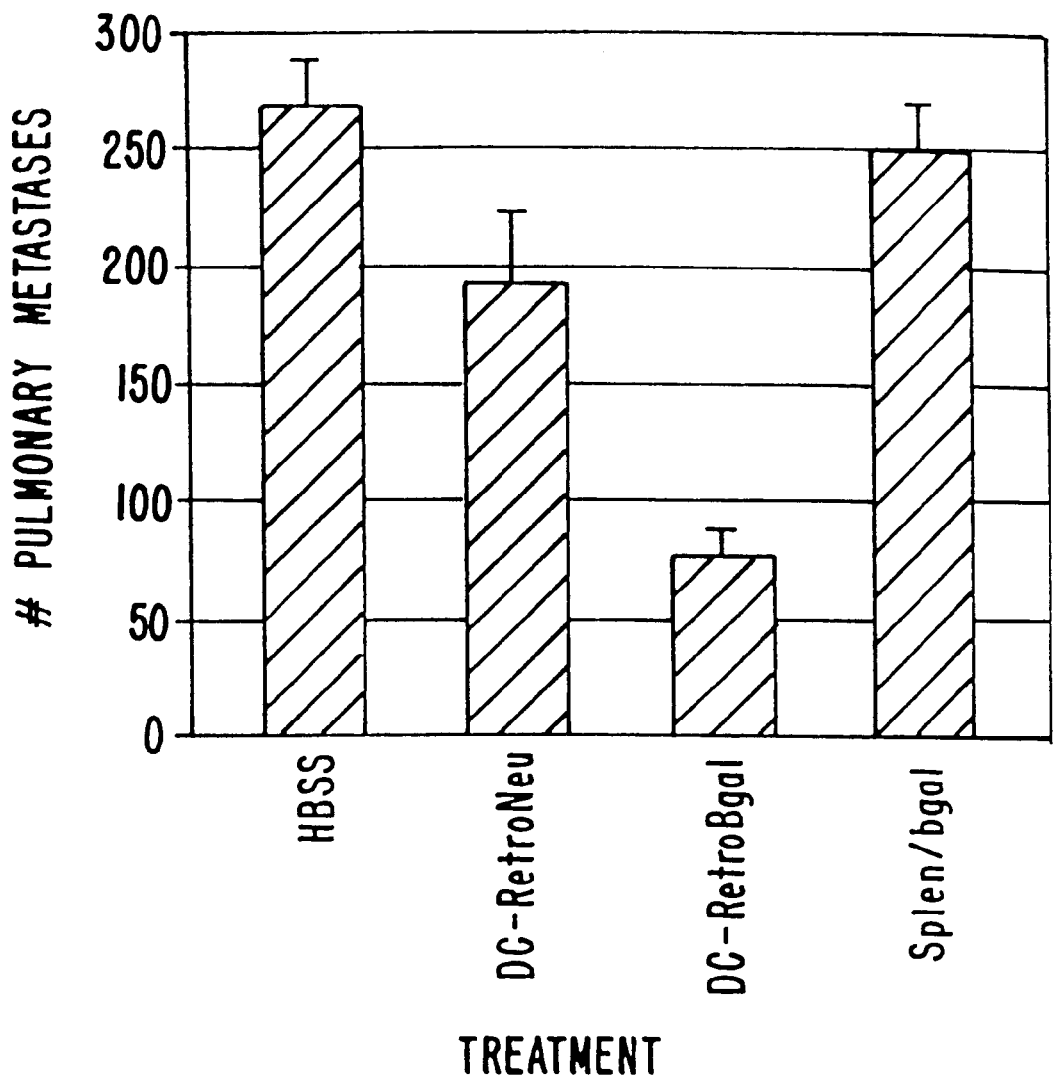
FIG. 6 is a bar graph showing that mice treated with βgal-transduced DC exhibited a significant reduction in pulmonary metastases compared to the control group.
Figure 7A:
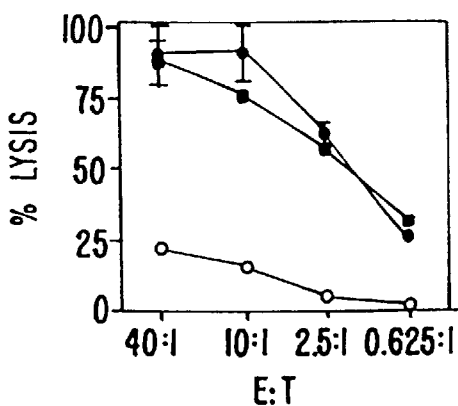
FIG. 7 shows Lysis of tumor and peptide-pulsed cells by lymphocytes stimulated with MART-transduced DCs. Autologous quiescent lymphocytes were stimulated with MART-transduced DCs (●) or SAM-transduced DCs (○). After two restimulations, the lymphocytes, or the positive control 1235 TIL (■), were tested for their ability to lyse various cells. Results are plotted as the mean percentage of lysis±SEM.
Figure 7B:
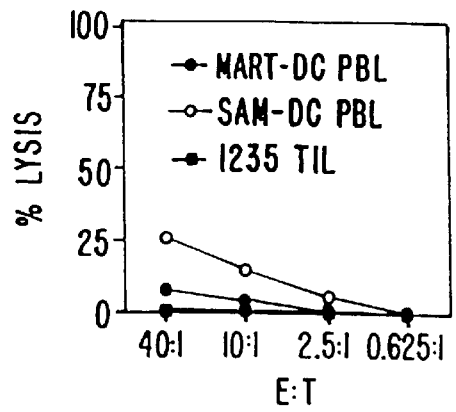
Figure 7C:
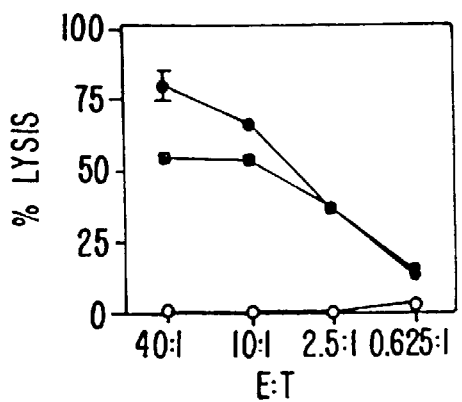
Figure 7D:
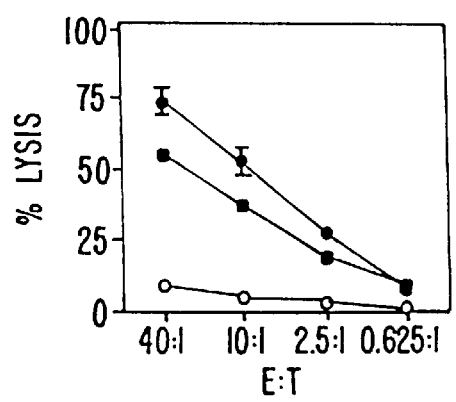
Figure 7E:
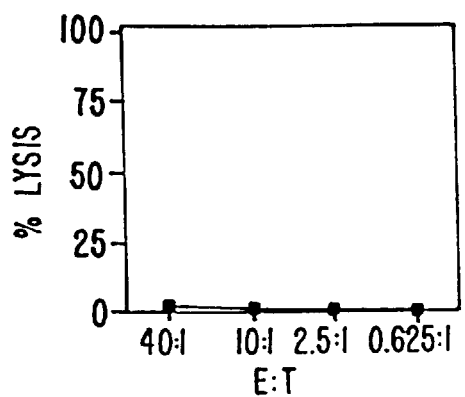
Figure 7F:
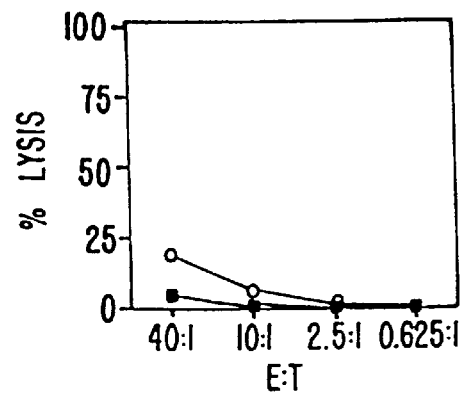

Dendritic cells were retrovirally transduced with the model tumor antigen β-galactosidase, or with a control retrovirus expressing the rat Neu gene. BALB/c mice were injected i.v. with 3×10$^5$ βgal-transduced CT26 tumor cells (C-25). Three and 6 days following tumor injection, mice were immunized with βgal- or neu-transduced dendritic cells. Twelve days following tumor injection, mice were sacrificed and pulmonary metastases were counted. Mice treated with βgal-transduced DC exhibited a significant reduction in pulmonary metastases compared to the control group (FIG. 6). In addition, βgal-specific T-cells were isolated from the spleens of mice immunized with βgal-transduced DC.

3-day Lung Met Model Summary:
D-0: BALB/c mice given 3×10$^5$ C25 (CT26/bgal) IV
D-3: Mice treated with 4×10$^5$ DC/mouse IV
D-6: Mice again treated with 4×10$^5$ DC/mouse IV
D-12: Lung mets counted Methods Cell Lines. CT26.CL25 (C-25) is a subclone of the CT26.WT, a BALB/c (H-2d) undifferentiated colon carcinoma stably transduced with a retrovirus encoding the lacZ gene. Cell lines were maintained in RPMI 1640 supplemented with 10% heat-inactivated fetal bovine serum, 2 mmol/L glutamine, 100 U/ml penicillin, 100 mg/ml streptomycin (all from Biofluids, Rockville Md.), 1.25 mg/ml amphotericin B (Fungizone; Life Technologies, Inc., Grand Island, N.Y.), and 50 mg/ml gentamicin sulfate (Life Technologies, Inc.) (CM). CT26.CL25 were maintained in the presence of 400 mg/ml G418 (Geneticin; Life Technologies, Inc.).

Bone Marrow-Derived Dendritic Cell Isolation. DC were prepared from bone marrow as described by Inaba et al., with some modifications. Briefly, bone marrow was flushed out from the long bones of the hind limbs and depleted of red cells with ACK lysing buffer (Biofluids). Bone marrow cells were depleted of lymphocytes and Ia+ cells using a mixture of rabbit anti-mouse lymphocyte serum and anti-mouse Iak alloantiserum, and rabbit complement (both from Accurate Chemical and Scientific Corp., Westbury, N.Y.). Cells were cultured in RPMI 1640 supplemented with 5% heat-inactivated fetal bovine serum, 2 mmol/L glutamine, 100 U/ml penicillin, 100 mg/ml streptomycin, 1.25 mg/ml amphotericin B, 50 mg/ml gentamicin sulfate, and 5×10−5 mM 2-mercaptoethanol (2-ME; Life Technologies, Inc.) supplemented with 20 ng/ml recombinant murine granulocyte-macrophage colony stimulating factor (rmGM-CSF) and 100 ng/ml recombinant murine interleukin 4 (rmIL-4) (both from Peprotech, Rocky Hill, N.J.). Cells were plated at 7×10$^5$ cells/ml with 5 ml/well in 6 well tissue culture plates containing the irradiated producer cells (see, below).

On day 2, cells were gently harvested to remove them from the adherent producer cells, pelleted, and replated in fresh medium containing IL-4 and GM-CSF, at 7×10$^5$ cells/ml with 5 ml/well in 6 well tissue culture plates. On day 4, 10 ng rmGM-CSF and 50 ng rmIL-4 were added to each well. On day 6, cells were harvested with gentle pipetting and replated in 100 mm tissue culture dishes 7×10$^5$ cell/ml with 10 ml/plate of DC CM supplemented with 20 ng/ml rmGM-CSF and 100 ng/ml rmIL-4. This method consistently yielded a cell population that was 30–50% by morphology and phenotype. On day 7, transduction and function of dendritic cells was confirmed using X-gal staining for β-galactosidase, mixed leukocyte reaction, and specific cytokine release using a β-gal-specific CTL clone.

Producer cells: Ecotropic producer cells were used containing the bgal gene or, as a control, the rat Neu gene under the transcriptional control of the LTR from Moloney murine leukemia virus (MMLV), using an MMLV backbone. Producer cells were irradiated with 5000 rads and plated at 5×105 cells per well in 6 well plates 24 hours prior to addition of murine bone marrow cells for co-cultivation. Producer cells were grown in DMEM/10% bovine calf serum.

In Vivo Treatment Studies: On day 0, 3×10$^5$ CT26.CL25 cells were injected i.v. into BALB/c mice to establish pulmonary metastases. On days 3 and 6, mice were immunized with transduced bone marrow-derived DC (4×105 IV). Mice were sacrificed on day 12 and metastatic lung nodules were enumerated in a randomized and blinded manner.

Statistical Analysis: The Wilcoxon-Mann-Whitney U test was used to examine the null hypothesis of identity of ranks between two sets of data.

Example 4

Gene Transfer into Human Dendritic Cells

Dendritic cells are highly potent antigen presenting cells that are capable of activating quiescent T cells, and which stimulate anti-tumor immune responses. Therefore, the ability constitutively to express tumor antigen genes in DC is a powerful method for characterizing new tumor antigens in vitro and to actively immunize in vivo. However, the growth of large numbers of DC has been difficult, and such cells have not been receptive to gene transfer. Since CD34$^+$ hematopoietic progenitor cells (HPC) can be differentiated into DC, human CD34$^+$ HPC were retrovirally transduced with tumor antigen genes, followed by in vitro differentiation into dendritic cells.

Human CD34+ HPC were retrovirally transduced with the marker gene murine B7-1 by four different methods, followed by differentiation in vitro into DC using GM-CSF, TNF-α, and SCF (see, supra). The four transduction methods were: 1) transduction with supernatant only (no co-culture), and amphotropic retrovirus (PA317); 2) transduction with co-culture with producer line, and amphotropic retrovirus (PA317); 3) transduction with supernatant only (no co-culture), and GaLV retrovirus (PG13); and, 4) transduction with co-culture, and GaLV retrovirus (PG13). Co-culture and GALV retrovirus improved transduction efficiency, as measured by expression of marker gene by FACS, more than 10 fold in the DC population compared to traditional supernatant and amphotropic transduction.

Human Dendritic Cell Studies: Hematopoietic progenitor cells were obtained from melanoma patients pretreated with G-CSF, followed by leukapheresis and isolation of CD34+ cells by positive selection on an antibody affinity column. These cells were successfully transduced with a marker gene as well as the MART-1 and GP100 tumor antigen genes. Following in vitro differentiation of the transduced cells into dendritic cells using GM-CSF and TNFα, 25–30% of B7-2+ dendritic cells expressed the marker gene on FACS analysis. Optimal dendritic cell transduction was obtained using co-cultivation with retroviral producer cells which utilize the gibbon ape leukemia virus (GALV) envelope (Table 6), as described supra.

TABLE 6

% Transduction of CD34+ Cells Differentiated to Dendritic Cells

| Retroviral Envelope | Method of Transduction | % of cells expressing marker gene | % of hB7-2+ cells expressing marker gene |
|---|---|---|---|
| Amphotropic (PA317) | Supernatant | 3 | 2 |
| | Co-culture | 12 | 8 |
| GALV (PG13) | Supernatant | 6 | 1 |
| | Co-culture | 38 | 28 |

Example 5

Transduction of Human Dendritic Cells with the MART-1 Melanoma Antigen Gene

Dendritic cells transduced with the MART-1 tumor antigen were recognized by MART-reactive tumor infiltrating lymphocytes (TIL), suggesting that the DC were capable of processing and presenting the foreign gene product (Table 7).

TABLE 7

Cytokine Release from MART-Reactive TIL in Response to Dendritic Cells Transduced with MART-1 (Tumor Antigen) Gene

| | Effectors [H IFNγ; pg/ml/24 hrs] | |
|---|---|---|
| Stimulators | None | TIL 1235 (MART-reactive T-cells) |
| None | 1 | 155 |
| Dendritic Cells | 3 | 230 |
| Dendritic Cells, transduced with control gene | 2 | 263 |
| Dendritic Cells, transduced with MART-1 | 4 | 1,855 |
| αCD3 (positive control) | 2 | 1,674 |

MART-1 transduced dendritic cells were able to stimulate the production of tumor-specific T-cells from resting lymphocytes. MART-specific T-cells were generated from resting lymphocytes using MART-transduced dendritic cells (Table 8).

Table 8: Cytokine Release from Lymphocytes
Stimulated with MART-Transduced Dendritic Cells
(hIFNγ; pg/ml/24 hours)

|  | Responders Lymphocytes stimulated with: | |
| --- | --- | --- |
| Stimulators | Control DC | MART DC |
| Media only | 22 | 16 |
| T2 + MART | 41 | 4395 |
| T2 + FLU | 48 | 20 |

Example 6

Transduction of Human Dendritic Cells with the GP100 Human Melanoma Antigen Gene GP100 transduced dendritic cells stimulated the production of tumor-specific T-cells from resting lymphocytes. GP100-specific T-cells were generated from resting lymphocytes using GP100-transduced dendritic cells (Table 9). Significant amounts of IFNγ were released when T-cells generated from GP100 transduced DC were co-cultured with T2 cells pulsed with A2-restricted GP100 peptide epitopes or with A2+ melanoma cells (624.38 mel and SK23 mel), but not with A2− melanoma cells (583 mel), or an A2+, GP100 breast tumor cell line (MDA 231).

TABLE 9

Cytokine Release from Lymphocytes Stimulated with GP100-
Transduced Dendritic Cells (hIFNγ; pg/ml/24/hrs)

|  |  | Responders Lymphocytes stimulated with: | |
| --- | --- | --- | --- |
| Stimulators | A2 | Control (Neo) DC | GP100 DC |
| Media only | N/A | 99 | 168 |
| T2 + FLU | + | 128 | 234 |
| T2 + M9-27 | + | 140 | 415 |
| T2 + G9-154 | + | 133 | 2980 |
| T2 + G9-209 | + | 160 | 228 |
| T2 + G9-280 | + | 124 | 2352 |
| 624.38 mel | + | 65 | 2414 |
| SK23 MEL | + | 36 | 797 |
| 583 MEL | − | 41 | 41 |
| MDA231 (breast cancer line) | + | 24 | 42 |

These studies demonstrated that tumor antigen genes were expressed by dendritic cells using retroviral transduction. Transduced dendritic cells are, therefore, valuable reagents for active immunization strategies against cancer and infectious diseases, and are useful in vitro to uncover unique tumor epitopes and antigens, and as a tool to study the basic biology of primary dendritic cells. Accordingly, metastatic melanoma patients are immunized with autologous dendritic cells transduced with the MART-1 or GP100 tumor antigen genes to inhibit melanoma metastasis and disease progression.

Example 7

Transduction of Human CD34+ HPC and Differentiation into DC

Human CD34+ HPC were retrovirally transduced with the melanoma tumor antigen gene MART-1 and differentiated in vitro into DC using GM-CSF, TNFα, and SCF (see, protocols). The MART-1 transduced DC have the same phenotypic and morphological characteristics and they have the same ability to stimulate allogeneic MLR as untransduced DC. In addition, the MART-1 transduced DC stimulated high levels of cytokine release by MART-1 specific tumor infiltrating lymphocytes (see, Table 10). This indicates that they were able to express, process, and present a MART-1 epitope on MHC class I molecules. This expression and presentation was stable, persisting beyond two weeks without selection.

TABLE 10

Cytokine Release from MART-reactive TIL in response to Dendritic Cells
Transduced with PG-SAM-MART-EN

|  | hIFN-γ (pg/ml/24 hr) Effectors | |
| --- | --- | --- |
| Targets | 0 | TIL 1235 |
| 0 | 2 | 130 |
| JDC | 0 | 226 |
| J p12-DC | 0 | 184 |
| J MART-DC | 4 | 2,604 |
| W p12-DC | 1 | 200 |
| W MART-DC | 0 | 1,237 |
| M p12 DC | 0 | 193 |
| M MART DC | 3 | 2,816 |
| SK23 | 0 | 19,670 |
| αCD3 | 0 | 4,301 |

J W and M represent 3 different patients; p12 is control DC transduced with unrelated gene Example 8

Stimulation of Autologous Peripheral Blood Lymphocytes with MART-1-transduced DCs Because the CD34+ HPCs that were transduced with MART-1 and differentiated to DCs were strongly recognized by MART-specific lymphocytes, it was of interest to determine whether the transduced DCs could stimulate quiescent autologous lymphocytes to raise a specific anti-MART CTL response. DCs were transduced with either the MART-1 or control SAM retrovirus, irradiated, and incubated with autologous quiescent T lymphocytes at a 1:10 stimulator-:effector ratio. The T cells were restimulated with freshly transduced DCs every two weeks and were tested for MART-1 reactivity one week after each stimulation. Specific cytokine release by lymphocytes against MART-1-expressing targets was not evident after the first restimulation. However, after two restimulations, the lymphocytes stimulated with MART-1-transduced DCs but not SAM-transduced DCs were highly MART-specific in one of three patients tested. Furthermore, they also released cytokine in response to HLA-A2+ melanoma cells that express MART-1, but not in response to HLA-A2− melanoma cells or HLA-A2+ non-melanoma tumor cells that do not express MART-1. The lymphocytes stimulated with MART-DC also exhibited strong and specific lysis of HLA-A2+ cells expressing MART-1 (FIG. 7). Both the MART-DC- and SAM-DC-stimulated lymphocytes proliferated well, expanding approximately 10-fold each week. These results indicate that CD34+ HPCs that are transduced with MART-1 and differentiated into DCs can stimulate the generation of specific anti-MART CTLs from autologous quiescent lymphocytes that are highly lytic and release large amounts of cytokine in response to HLA-matched MART peptide-pulsed cells and melanoma cells.

DCs were transduced with either the MART-1 or control SAM retrovirus as described supra, irradiated (1500 cGy), and incubated with autologous quiescent T lymphocytes at a 1:10 stimulator:effector ratio. IL-2 (300 IU/ml) was added on day 2. The T cells were restimulated with freshly transduced DCs in this manner every two weeks and were tested for MART-1 reactivity one week after each stimulation. After two restimulations, the lymphocytes were tested for their ability to recognize various cells. These cells included T2 cells pulsed either with the $MART_{27-35}$ or irrelevant influenza M1 peptide, the HLA-A2$^+$ melanoma lines 624.38 mel and SK23 mel, the HLA-A2$^-$ melanoma line 586 mel, and the HLA-A2$^+$ breast cancer line MDA231, which does not express MART-1. OKT3 is a positive control in which the plate is coated with antibody against the T-cell receptor complex. Results are expressed as the mean±SEM.

TABLE 11

Cytokine Release from Lymphocytes Stimulated With Mart-Transduced DCs.

| | | Responders | | |
|---|---|---|---|---|
| Stimulators | None | SAM-DC PBL | MART-DC PBL | 1235 TIL |
| 0 | 0 ± 0.05$^a$ | 22 ± 2 | 16 ± 1 | 94 ± 4 |
| T2 + MART | 0 ± 0.06 | 41 ± 1 | 4400 ± 300 | 2800 ± 100 |
| T2 + FLU | 3 ± 0.1 | 48 ± 2 | 20 ± 2 | 45 ± 0.4 |
| 624.38 mel | 0 ± 0.01 | 9 ± 0.2 | 702 ± 2 | 2500 ± 200 |
| SK23 mel | 0 ± 0.06 | 6 ± 0.3 | 1400 ± 100 | 5400 ± 200 |
| 586 mel | 1 ± 0.1 | 10 ± 0.8 | 18 ± 1 | 29 ± 3 |
| MDA231 | 0 ± 0.04 | 5 ± 0.1 | 7 ± 0.1 | 104 ± 7 |
| OKT3 | 0 ± 0.09 | 1200 ± 100 | 660 ± 30 | 2000 ± 200 |

$^a$Human INF-τ (pg/ml/24 h).

Protocols

Retroviruses and Packaging Lines

All retroviral constructs are based on the SAM-EN construct (*Blood* (1995) 85:139–145). In brief, the gene of interest (murine B7-1, beta-galactosidase, MART-1) was cloned into the multiple cloning site of the retroviral plasmid pSAMEN. The amphotropic retroviral producer lines were constructed by a micro-ping-pong technique involving transfection of the retroviral plasmid into a mixture of PA317 (amphotropic) (*Mol. Cell. Biol.* (1986) 6:2895–2902) and GP+E86 (ecotropic) (*J. Virol* (1988) 62:1120) packaging cell lines, followed by overgrowth of the amphotropic line. The Gibbon Ape leukemia virus (GaLV) retroviral producer lines were constructed by transduction of the PG13 (Gibbon Ape) (J. Virol. (1991) 65:2220–2224) packaging line with supernatant from the appropriate amphotropic producer cells.

Isolation of Human CD34+ HPC

Patients were treated with G-CSF for 5 days, followed by leukapheresis. CD34+ cells were selected using an immunoaffinity column from CellPro (Bothell, Wash.) according to the manufacturer's directions. CD34+ cells were washed with PBS and cryopreserved in 90% human male AB serum (Sigma, St. Louis) and 10% DMSO.

Transduction of Human CD34+ HPC and Differentiation into Dendritic Cells

1. Thaw CD34$^+$ cells: On day 0, CD34$^+$ cells thawed into 20 ml CM, counted, centrifuged (2000 rpm, RT), resuspended in 5 ml DC CM in 6 well plates at 5×10$^5$ cells/well.
2. Transduction: On day 1, cells transduced for 6 hrs by resuspending cells (2000 rpm, RT) in 2.5 ml CM containing 2×DC cytokines and polybrene (1×polybrene=8 mg/ml). 2.5 ml of retroviral supernatant (see b below) combined with cell suspension in 6 well plate that has irradiated producer line monolayer (see a below). Plates centrifuged (2500 rpm, 32° C., 1 hr), and incubated for 5 hrs in CO2 incubator at 37° C. Transduction stopped by resuspending cells (2000 rpm, RT) in 5 ml DC CM, and incubating 18 hrs in CO$_2$ incubator at 37° C. This completes one transduction cycle.

a. Production of Co-Culture Monolayer Producer cell line (PA317 or PG13-based) harvested by trypsinization, irradiated to 3000 rads. Irradiated cells plated at 7×10$^5$ cells/well in supernatant CM in 6 well plates the night before transduction. If the irradiated producer cells look ragged, fresh monolayers of irradiated producer cells were made in new wells for each cycle of transduction. Typically, one monolayer was used for the first two transduction cycles, and a new monolayer was used for the third cycle (to balance cell loss from transferring to new monolayers with the monolayer being in good shape).

b. Production of Supernatant: Retroviral producer lines grown to near-confluency in T-175 flasks. Medium removed, and 30 ml supernatant CM replaced. Flasks were then incubated for 12–16 hrs in CO$_2$ incubator at 32° C. Medium removed and filtered through 0.45 mm filter, and then either used directly or refrigerated (never more than 3 days) until use.

3. Retransduction: On days 2 and 3, cells transduced a second and third time by repeating the transduction cycle outlined in #2 above.
4. Cell Growth: Cells grown in 5 ml/well DC CM (in 6 well plate) until day 12 when they are used. ½ medium changed, and nonadherent cells transferred to new plates on day 8. Notes: 1. CM=[Iscove's medium+10% hu AB, abx, gln], except during the six hours of transduction in the three cycles—then 10% FCS is used in place of 10% hu AB.2. DC CM=CM with GM-CSF (100 ng/ml), TNF-α (100 ng/ml), and SCF (20 ng/ml; activity: ED50= 2.5 ng/ml) 3. Supernatant CM=DM EM +10% FBS, abx, gln.

MLR Assay

Allogeneic T cells were prepared from PBMC by negative selection on an TCC-1000 immunoaffinity column according to the manufacturer's instructions (R&D, Minneapolis, Minn.). Allogeneic PBMC or DC from the same donor were irradiated to 1500 rad. T cells (1.5×10$^5$) were added to flat bottom 96 well plates, along with varying numbers of irradiated PBMC or DC. Four days later, the cells were pulsed with 1 mCi [$^3$H]thymidine, and cell proliferation was estimated 8 hours later by measuring the incorporation of radioactivity into DNA (Betaplate, Pharmacia LKB, Gaithersburg, Md.).

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications are made thereto without departing from the spirit or scope of the appended claims.

What is claimed is:

1. A method of making a mammalian dendritic cell transduced with a selected nucleic acid, comprising:
   transducing a mammalian hematopoietic stem cell in vitro with the selected nucleic acid; and
   differentiating the transduced stem cell with the selected nucleic acid, thereby making a dendritic cell transduced with the selected nucleic acid.

2. The method of claim 1, wherein the stem cell is a CD34+ stem cell.

3. The method of claim 1, wherein the stem cell is a CD34+ stem cell, wherein the stem cell is negative for MHC class II antigens.

4. The method of claim 1, wherein the stem cell is differentated into a dendritic cell in vitro, wherein the stem cell is differentiated into a dendritic cell by contacting the stem cell with lipofectamine and a cytokine selected from the group consisting of murine GM-CSF, human GM-CSF, IL4, SCF, Flt3, and TNF-α, and wherein the method further comprises tirrating the cytokines to determine the concentration of the cytokine which provides optimal differentiation.

5. A method of activating a T cell, comprising contacting the T cell with a dendritic cell, wherein the dendritic cell expresses a heterologous protein in antigen encoded by a recombinant nucleic acid, wherein the recombinant nucleic acid is expressed in the dendritic cell.

6. The method of claim 5, wherein the dendritic cell contacts the T cell in vitro.

7. The method of claim 5, wherein the heterologous protein antigen comprises a peptide subsequence derived from a peptide expressed on the surface of a cancer cell.

8. The method of claim 7, wherein the activated T cell is competent to kill the cancer cell.

9. A recombinant dendritic cell comprising a recombinant expression cassette, wherein
   (i) the recombinant expression cassette encodes an antigenic peptide, and
   (ii) the recombinant expression cassette was transduced into a stem cell using a retroviral vector, which stem cell was differentiated into the dendritic cell.

10. A recombinant dendritic cell comprising a recombinant expression cassette, wherein (i) the recombinant expression cassette encodes an antigenic peptide, and (ii) the antigenic peptide is encoded in the expression cassette as a subsequence of a full length protein encoded by the expression cassette.

11. A recombinant dendritic cell comprising a recombinant expression cassette, wherein (i) the recombinant expression cassette encodes an antigenic peptide, and (ii) the antigenic peptide is derived from a protein selected from the group of antigenic proteins consisting of HER-2, MART-1, gp-100, PSA, HBVc, HBVs, tyrosinases, MAGE-1, trp-1 and CEA.

12. A recombinant dendritic cell comprising a recombinant expression cassette, wherein (i) the recombinant expression cassette encodes an antigenic peptide, and (ii) the recombinant cell further comprises a recombinant expression cassette encoding a cytokine.

13. A recombinant dendritic cell comprising a recombinant expression cassette, wherein (i) the recombinant expression cassette encodes an antigenic peptide, and (ii) the recombinant cell further comprises a recombinant expression cassette encoding a cytokine selected from the group consisting of GM-CSF, IL-2, and TNF.

14. A recombinant dendritic cell comprising a recombinant expression cassette, wherein (i) the recombinant expression cassette encodes an antigenic peptide, and (ii) the recombinant cell further comprises a recombinant expression cassette encoding a cell receptor ligand.

15. A recombinant dendritic cell which comprises a recombinant expression cassette, which expression cassette encodes a protein selected from the group consisting of a cytokine, a cell receptor ligand, and, a subsequence of a cytokine protein.

16. The recombinant dendritic cell of claim 15, wherein the cell further comprises an antigenic peptide.

17. The recombinant dendritic cell of claim 15, wherein the cell further comprises an antigenic peptide derived from a protein selected from the group of antigenic proteins consisting of HER-2, MART-1, gp100, PSA, HBVc, HBVs, tyrosinase, MAGE-1, trp-1 and CEA.

18. A cell culture for making recombinant mammalian dendritic cells comprising a mammalian hematopoietic stem cell transduced with a recombinant nucleic acid encoding an antigen, and GM-CSF.

19. The cell culture of claim 18, wherein the GM-CSF is selected from the group consisting of murine GM-CSF, and human GM-CSF.

20. The cell culture of claim 18, further comprising a cytokine selected from the group consisting of TNF-α, SCF, Flt3 and IL4.

21. The cell culture of claim 18, wherein the GM-CSF is provided at a concentration of at least about 2 ng/ml.

22. The cell culture of claim 18, wherein the GM-CSF is provided at a concentration of at least about 20 ng/ml.

23. The cell culture of claim 18, wherein the GM-CSF is provided at a concentration of at least about 100 ng/ml.

24. The cell culture of claim 18, wherein the GM-CSF is provided at a concentration of between 20 ng/ml and about 200 ng/ml, and wherein the culture further comprises a second cytokine selected from the group consisting of TNF-α, SCF, Flt3 and IL-4, wherein the concentration of the second cytokine is between about 20 ng/ml and 200 ng/ml.

25. The cell culture of claim 18, wherein the recombinant stem cell is a recombinant human $CD34^+$ stem cell.

26. A pharmaceutical composition comprising a pharmaceutically acceptable carrier and a recombinant dendritic cell which expresses a heterologous protein antigen, which recombinant dendritic cell is competent to activate a T cell to kill a target cell in vivo.

27. The pharmaceutical composition of claim 26, wherein the heterologous protein antigen is selected from the group of proteins consisting of HER-2, MART-1, gp-100, PSA, HBVc, HBVs, tyrosinase, MAGE-1, trp-1 and CEA.

28. The pharmaceutical composition of claim 26, further comprising a T cell.

29. The pharmaceutical composition of claim 26, wherein the heterologous protein antigen is a tumor antigen, and wherein the target cell is a cancer cell.

30. The method of claim 1, wherein the dendritic cell transduced with the selected nucleic acid expresses a protein encoded by the selected nucleic acid.

31. The method of claim 30, wherein the expressed protein is presented by the dendritic cell on the cell surface.

32. The method of claim 31, wherein the expressed protein is presented by the dendritic cell in conjunction with a molecule of the major histocompatibility complex (MHC).

33. The method of claim 32 wherein the expressed protein is presented by the dendritic cell bound to a molecule of the major histocompatibility complex (MHC).

34. The method of claim 30, further comprising contacting the dendritic cell with a T cell, wherein the protein expressed by the dendritic cell is a protein antigen.

35. The method of claim 34 wherein said contacting activates the T cell to recognize cells expressing the protein antigen expressed by the dendritic cell from the selected nucleic acid.

36. The method of claim 30, further comprising contacting the dendritic cell with a resting lymphocyte, wherein the protein expressed by the dendritic cell is a protein antigen.

37. The method of claim 36, wherein the resting lymphocyte produces T cells specifically activated by the protein expressed by the dendritic cell from the selected nucleic acid.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
       (A) LENGTH: 800 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..800
       (D) OTHER INFORMATION: /note= "MART-1 melanoma tumor antigen"

(xi) SEQUENCE DESCRIPTION: SEQ ID NO: 1:

| | | | | | | |
|---|---|---|---|---|---|---|
| TNAGGATGTC | GTCAAGAAGA | AGNGCCAGGT | TTCCGGGCCT | CACATTGNCA | NAAGACGGGA | 60 |
| ATATGGTGGA | TAGACAAACG | CACACCGGCC | TTATTCCAAG | CGGNTTCGGC | CAGTAACGTT | 120 |
| AGGGGGGGGG | GGGAATTGAT | CCCGCTCGAA | CTGCTAGCGG | ACCTACTAAA | ATTTTAACAC | 180 |
| TGACTTATTA | TTAGAGATGG | NTTGNATTTT | TCCTACACCA | TTCCAAAGGA | GAACATTAGA | 240 |
| TGTCTGTATT | AAATTCAAGC | AAAAGTGTGA | GAGAAATAAT | TTCAGCATGT | CTCAGGTGTC | 300 |
| TCGCTGGCTC | TTAAGGTGAA | TAAGGTGGTG | GTGACTGTTC | TGCAGAGAGT | TTCTCATAAG | 360 |
| CAGGTGGAGC | ATTGGGAACA | CAGGTTCACA | GNTTTTCTCT | TGAAGAGACA | CTTTGNTGTC | 420 |
| CCNATGATCA | AACCCTTCTT | GTGGGCATCT | TCTTGTTAAG | GCACATTGAG | TGNCACATGA | 480 |
| AGACTTTTAT | CCATCAAGGG | TCTGTATCCA | TTCGGCTTCT | TCAATACCAC | AGCCCATGAG | 540 |
| CAGGAAGATC | CAGGNCACTG | TCAAGATGCC | GTCCCNGNGG | GCTCTCCANC | NNNGNGTAAG | 600 |
| AGTGCCCNGC | CCCTCTTGGG | GNACCATGGT | GAAGGGAGAT | TTCTCTTNGA | TNTNTGGGGC | 660 |
| AAAGGANAAG | AAACCCCCTN | ATANAGNCCC | TTCTTTTNNC | GGATGGGAAT | NGCCCCGAGG | 720 |
| GNCCCCCGNT | TCGTGGGGCC | NCNAANNTNG | AGGTTGGCCC | CCCCCGGGTG | GGAAGCTNCA | 780 |
| CNTNGGGGGG | NNTTTCCCCN | | | | | 800 |